(12) United States Patent
Bennett et al.

(10) Patent No.: US 8,626,302 B2
(45) Date of Patent: Jan. 7, 2014

(54) SYSTEMS AND METHODS TO PLACE ONE OR MORE LEADS IN MUSCLE FOR PROVIDING ELECTRICAL STIMULATION TO TREAT PAIN

(75) Inventors: Maria E. Bennett, Beachwood, OH (US); Geoffrey B. Thrope, Shaker Heights, OH (US); Joseph W. Boggs, II, Carrboro, NC (US); Andreas Inmann, Cleveland, OH (US); John Chae, Strongsville, OH (US)

(73) Assignee: SPR Therapeutics, LLC, Cleveland, OH (US)

( * ) Notice: Subject to any disclaimer, the term of this patent is extended or adjusted under 35 U.S.C. 154(b) by 506 days.

(21) Appl. No.: 12/462,371

(22) Filed: Aug. 3, 2009

(65) Prior Publication Data

US 2010/0036454 A1    Feb. 11, 2010

Related U.S. Application Data

(60) Continuation-in-part of application No. 11/982,789, filed on Nov. 5, 2007, now Pat. No. 8,249,713, which is a continuation of application No. 10/867,396, filed on Jun. 14, 2004, now abandoned, which is a division of application No. 10/138,791, filed on May 3, 2002, now Pat. No. 6,845,271, which is a continuation-in-part of application No. 09/862,156, filed on May 21, 2001, now abandoned, which is a continuation of application No. 09/089,994, filed on Jun. 3, 1998, now abandoned.

(60) Provisional application No. 61/137,652, filed on Aug. 1, 2008, provisional application No. 61/201,116, filed on Dec. 5, 2008.

(51) Int. Cl.
*A61N 1/04* (2006.01)

(52) U.S. Cl.
USPC .............................................. 607/46; 607/48

(58) Field of Classification Search
USPC ................................................ 607/48–50, 46
See application file for complete search history.

(56) References Cited

U.S. PATENT DOCUMENTS

| 2,521,722 | A | 9/1950 | Hubbell et al. |
| 3,067,401 | A | 12/1962 | Rhodes |

(Continued)

FOREIGN PATENT DOCUMENTS

| EP | 0 165 049 | 12/1985 |
| GB | 945482 | 1/1964 |

(Continued)

OTHER PUBLICATIONS

PCT Notice of Transmittal of International Preliminary Report on Patentability; PCT/US09-04441; Oct. 12, 2010.

(Continued)

*Primary Examiner* — Joseph Stoklosa
(74) *Attorney, Agent, or Firm* — McDonald Hopkins LLC

(57) ABSTRACT

Systems and methods are adapted to provide the relief of pain. The systems and methods make possible the percutaneous placement of one or more intramuscular leads, without the need for fluoroscopy, for providing electrical stimulation to activate a motor point innervating the muscle, to provide the therapeutic relief of pain. The one or more intramuscular leads may be placed in muscle(s) to resist migration. The target nerves and their motor points innervate the muscles in which the one or more leads are placed. The systems and methods can include a two-stage solution. The first stage may include temporary systems and methods, including the use of an external pulse generator. The second stage may include more permanent systems and methods, including the use of an implanted pulse generator.

12 Claims, 10 Drawing Sheets

(56) References Cited

U.S. PATENT DOCUMENTS

| | | | |
|---|---|---|---|
| 3,568,675 A | 3/1971 | Harvey | |
| 3,663,965 A | 5/1972 | Lee, Jr. et al. | |
| 3,701,080 A | 10/1972 | Baisz et al. | |
| 3,850,161 A | 11/1974 | Liss | |
| 3,964,470 A | 6/1976 | Trombley | |
| 4,019,518 A * | 4/1977 | Maurer et al. | 607/59 |
| 4,026,301 A | 5/1977 | Friedman et al. | |
| 4,223,679 A | 9/1980 | Schulman et al. | |
| 4,250,882 A | 2/1981 | Adair | |
| 4,281,664 A | 8/1981 | Duggan | |
| 4,326,534 A | 4/1982 | Axelgaard et al. | |
| 4,408,608 A | 10/1983 | Daly et al. | |
| 4,413,314 A | 11/1983 | Slater et al. | |
| 4,453,162 A | 6/1984 | Money et al. | |
| 4,459,989 A | 7/1984 | Borkan | |
| 4,528,984 A | 7/1985 | Morawetz et al. | |
| 4,528,987 A | 7/1985 | Slocum | |
| 4,532,932 A | 8/1985 | Batty, Jr. | |
| 4,558,704 A | 12/1985 | Petrofsky | |
| 4,561,443 A | 12/1985 | Hogrefe et al. | |
| 4,569,352 A | 2/1986 | Petrofsky et al. | |
| 4,579,120 A | 4/1986 | MacGregor | |
| 4,586,510 A | 5/1986 | Glaser et al. | |
| 4,595,010 A | 6/1986 | Radke | |
| 4,622,973 A | 11/1986 | Agrawala | |
| 4,632,116 A | 12/1986 | Rosen et al. | |
| 4,639,667 A | 1/1987 | Andresen | |
| 4,640,983 A | 2/1987 | Comte | |
| 4,645,504 A | 2/1987 | Byers | |
| 4,690,145 A | 9/1987 | King-Smith et al. | |
| 4,693,254 A | 9/1987 | Mickiewicz et al. | |
| 4,699,143 A | 10/1987 | Dufresne et al. | |
| 4,793,353 A | 12/1988 | Borkan | |
| 4,942,514 A | 7/1990 | Miyagaki et al. | |
| 4,990,258 A | 2/1991 | Bjare et al. | |
| 5,041,974 A * | 8/1991 | Walker et al. | 607/63 |
| 5,063,929 A | 11/1991 | Bartelt et al. | |
| 5,167,229 A * | 12/1992 | Peckham et al. | 607/48 |
| 5,247,434 A | 9/1993 | Peterson et al. | |
| 5,285,781 A | 2/1994 | Brodard | |
| 5,300,096 A | 4/1994 | Hall et al. | |
| 5,405,367 A * | 4/1995 | Schulman et al. | 607/61 |
| 5,581,687 A | 12/1996 | Lyle et al. | |
| 5,609,770 A | 3/1997 | Zimmerman et al. | |
| 5,653,887 A | 8/1997 | Wahl et al. | |
| 5,702,428 A | 12/1997 | Tippey et al. | |
| 5,769,875 A * | 6/1998 | Peckham et al. | 607/48 |
| 5,800,458 A | 9/1998 | Wingrove | |
| 5,836,995 A | 11/1998 | MGraw et al. | |
| 5,861,017 A | 1/1999 | Smith et al. | |
| 5,983,140 A | 11/1999 | Smith et al. | |
| RE36,690 E | 5/2000 | McGraw et al. | |
| 6,163,725 A | 12/2000 | Peckham et al. | |
| 6,315,721 B2 | 11/2001 | Schulman et al. | |
| 6,532,390 B1 * | 3/2003 | Chu et al. | 607/116 |
| 2004/0122482 A1 | 6/2004 | Tung et al. | |
| 2004/0186532 A1* | 9/2004 | Tadlock | 607/48 |
| 2007/0255340 A1 | 11/2007 | Giftakis et al. | |
| 2008/0065171 A1 | 3/2008 | Fang et al. | |
| 2008/0077192 A1* | 3/2008 | Harry et al. | 607/48 |
| 2009/0054952 A1* | 2/2009 | Glukhovsky et al. | 607/61 |
| 2009/0099612 A1* | 4/2009 | Armstrong | 607/3 |
| 2009/0326602 A1* | 12/2009 | Glukhovsky et al. | 607/41 |
| 2010/0198298 A1* | 8/2010 | Glukhovsky et al. | 607/46 |

FOREIGN PATENT DOCUMENTS

| | | |
|---|---|---|
| GB | 2 085 733 | 5/1982 |
| GB | 2 123 698 | 2/1984 |
| GB | 2 223 949 | 4/1990 |

OTHER PUBLICATIONS

NeuroControl Press Release (Jan. 17, 2000) StIM (TM) Receives CE Mark Approval.

NeuroControl StIM (TM) System Brochure; circa Jan. 2000.

The NeuroControl StIM (TM) System Brochure; circa Jan. 2000.

Prochazka et al., "Remote Monitoring . . . in Unrestrained Cats", Electroencephalogrphy & Clin. Neurophysiology, vol. 37, No. 6, Dec. 1974, pp. 649-653.

Vodovnik et al., "Electronic Detours of Broken Nerve Paths", Electronics, Sep. 20, 1965; pp. 110-116.

Maass et al., "Mobility Aid for Quadriplegics", Carnahan Conference on Electronic Prosthesis, Lexington, KY, Sep. 19-21, 1973; pp. 123-125.

Leob et al., "Design and Fabrication for Experimental Cochlear Prosthesis", Med & Biomed Eng. & Compute. May 1983, pp. 241-253.

Peckham et al., "Restoration of Hand Function in the Quadriplegic Through Electrical Stimulation", Functional Electrical Stimulation, Hanbrecht & Reswick, 1977, pp. 83-95.

Smith et al., "A Portable Microprocessor Controlled Implantable Functional Neuromuscular Stimulation System", Proceedings of the 2nd Int. Conf. on Rehab, Eng. 1984.

Buckett et al., "A Microprocessor Based Portable Functional Electrical Stimulation System", Annual Conference on Rehabilitation Eng., San Diego, CA 1983, pp. 72-74.

Forster, "Theoretical Design & Implementation of a Transcutaneous, Multichannel Stimulator for Neural Prosthesis Applications", J. Biomed. Eng. vol. 3, No. 2, Apr. 1981; pp. 107-120.

Buckett et al., "Shoulder Position Control, An Alternative Control Technique for Motion Impaired Individuals", Proceed of Int'l Conf. on Rehab. Eng., Toronto 1980, pp. 224-247.

Peckham et al., "Multichannel Implantable Stimulator for Control of Paralyzed Muscle", IEEE Trans on Biomed. Eng. V. BME, 1981.

Thrope et al., "A Proportional Joystick Controller for High Level Quadriplegics", RESNA 8th Annual Conference, Memphis, TN 1985, pp. 401-403.

Paeslack et al., "Design and Control of a Manipulator for Tetraplegics", Mechanism & Machine Theory, 1977, vol. 12, No. 5, pp. 413-423.

Hansen, "EMG Controlled Functional . . . of the Paretic Hand", Scan. J. Rehab Med. Nov. 1979, pp. 189-193.

Strojnkik et al., "Programmed Six Channel . . . During Walking", IEEE Trans. on Biomed. Eng. vol. BME:26 2, Feb. 1979; pp. 112-116.

Rebersek et al., "Proportionally Controlled Functional Electrical Stimulation of the Hand", ArchPhys Med Rehab. vol. 54, Aug. 1973, pp. 378-382.

Thrope et al., "A Computer Controlled . . . Functional Neuromuscular Stimulation", IEEE Transactions on Bio Eng. vol. BME-32, No. 6, Jun. 1985, pp. 363-370.

Peckham et al., "Controlled Prehension and Release . . . Forearm Musculature", Annals of Biomedical Engineering, 1980, vol. 8, pp. 368-388.

Peckham et al., "Restoration of Key Grip . . . Electrical Stimulation", Proceedings of Intern. Conf. on Rehab. Eng., Toronto Canada, 1980, pp. 227-229.

Peckham et al., "Alteration in the Force . . . Electrical Stimulation", Clinical Orthopaedics & Related Research, No. 114, Jan.-Feb. 1976, pp. 326-344.

Crago, "Control of Movements by Functional Neuromuscular Stimulation", Eng. in Med & Biol. Magazine, Sep. 1983, pp. 32-36.

Crago et al., "Closed Loop Control . . . Stimulation of Muscle", IEEE Transactions on Bio Eng., vol. MBE-27, No. 6, Jun. 1980, pp. 306-312.

Poon et al., "An Implantable RF-Powered Dual Channel Stimulator", Biotelemetry Patient Monitoring, vol. 8 No. 3, pp. 180-188 (1981).

Peckham et al., "Coordinated Two Mode Grasp in the Quadriplegic . . . Neuromuscular Stimulation", IFAC Control Aspects of Prosthetics & Orthotics, Ohio USA 1, 1982.

Chae et al., Neuromuscular Stimulation for Upper Extremity Motor and Functional Recovery in Acute Hemiplegia, Stroke, 29,, 975-979, 1998.

Caldwell et al., A Percutaneous Wire Electrode for Chronic Research Use, IEEE Transactions on Biomedical Engineering, pp. 429-432, Sep. 1975.

(56) References Cited

OTHER PUBLICATIONS

Brooke et al., Shoulder Subluxation in Hemiplegia: Effects of Three Different Supports, Arch Phys Med Regahil vol. 72, Jul. 1991.
Bohannon et al., Shoulder Pain in Hemiplegia: Statistical Relationship with Five Variables, Arch Phys Med Rehabil, vol. 67, Aug. 1986.
Bigeleisen et al., Extraneural versus Intraneural Stimulation Thresholds during Ultrasound-guided Supraclavicular Block, Anesthesiology, 110, 1235-43, 2009.
Bhakta et al., Use of botulinum toxin in stroke patients with severe upper limb spasticity, Journal of Neuroloy, Neurosurgery, and Psychiatry, 61, 30-35, 1996.
Bhadra et al., Extraction Forces and Tissue Changes During Explant of CWRU-Type Intramuscular Electrodes from Rat Gastrocnemius, Annals of Biomed Eng, vol. 25, 1017-1025, 1997.
Bernstein et al, Spinal Cord Stimulation in Conjunction with Peripheral Nerve Field Stimulation . . . , Neuromodulation; Technology at the Neural Interface, vol. 11 No. 2 2008.
Bates et al., Veterans Affairs/Dept of Defense Clinical Practice Guideline for the Management of Adult Stroke Rehabilitation Care . . . Stroke, pp. 2049-2056 Sep. 2005.
Baker et al. Effects of Waveform on Comfort During Neuromuscular Electrical Stimulation, Clinical Orthopaedics and Related Research, No. 233, pp. 75-85 Aug. 1988.
Baker at al., Neuromuscular Electrical Stimulation of the Muscles Surrounding the Shoulder, Physical Therapy, vol. 66, No. 12, pp. 1930-1937, Dec. 1986.
Anderson et al., Validation of the Short Form 36 (SF-36) Health Survey Questionnaire Among Stroke Patients, Stroke, 27, 1812-1816, 1996.
C. Anderson, Complications in Spinal Cord Stimulation for Treatment of Angina Pectoris, Acia Cardiologica, vol. LII, 4, pp. 325-333, 1997.
Peckham et al., Coordinated Two Mode Grasp in the Quadriplegic Initiated by Functional Neuromuscular Stimulation, IFAC Control Aspects of Prosthetics and Orthotics, 1982.
Chae et al., Percutaneous, Intramuscular Neuromuscular Electrical Stimulation for the Treatment of Shoulder.., Am J Phys Med Rehabil, vol. 80, No. 4, pp. 296-301, Apr. 2001.
Finsen et al., Transcutaneous Electrical Nerve Stimulation after Major Amputation, The Journal of Bone and Joint Surgery, vol. 70-B, No. 1, pp. 109-112, Jan. 1988.
Chae et al., Intramuscular Electrical Stimulation for Hemiplegic Shoulder Pain, Am. J. Phys. Med. Rehabil., vol. 84, No. 11, pp. 832-842, Nov. 2005.
Chantraine et al., Should Pain and Dysfunction in Hemiplegia: Effects of Functional Electrical Stimulation, arch Phys Med Rehabil vol. 80, pp. 328-331, Mar. 1999.
Chae et al, Poststroke Shoulder Pain: Its Relationship to Motor Imparient, Activity Limitation, and Quality of Life, Arch Phys Med Rehabil, vol. 88, pp. 298-301, Mar. 2007.
Chae et al, Subacromial Corticosteroid Injection for Poststroke Shoulder pain: A Retrospective Chart Review, Arch Phys Med Rehabil, vol. 88, pp. 1890-1693, Dec. 2007.
Cleeland et al., Pain Assessment: Global Use of the Brief Pain Inventory, Annals Academy of Medicine, vol. 23, No. 2, pp. 129-138, Mar. 1994.
Faghri et al., The effects of functional electrical stimulation on shoulder subluxation, arm function recovery,.., Arch Phys Med Rehabil, vol. 75, pp. 73-79, Jan. 1994.
Chung et al., Factors influencing peripheral nerve stimulation produced inhibition of primate spinothalamic tract cells, Pain, 19, pp. 277-293, 1984.
Checcucci et al., A new technique for regional anesthesia for arthroscopic shoulder surgery based . . . , J Arthroscopic & Related Surgery, vol. 24, No. 6, pp. 689-696, Jun. 2008.
Dorman et al, Qualitative Comparison of the reliability of health status assessments with the EuroQol and SF-36.., Stroke, 29, pp. 63-68, 1998.

Farrar et al, Clinical importance of changes in chronic pain intensity measured on an 11-point numerical pain rating scale, Pain, 94, pp. 149-158, 2001.
Chae et al., Intramuscular electrical stimulation for shoulder pain in Hemiplegia: Does time from stroke onset predict . . . , Neurorehabil Neural Repair, 21, pp. 561-567, 2007.
Gamble et al, Poststroke shoulder pain: a prospective study of the association and risk factors in 152 patients . . . , European J of Pain, 6, pp. 467-474, 2002.
Goldman et al, Dorsal Genital Nerve Stimulation for the Treatment of Overactive Bladder Symptoms, Neurourology and Urodynamics, 27(6), pp. 499-503, 2008.
Gamble et al., Post stroke shoulder pain: more common than previously realized, European J of Pain, 4, pp. 313-315, 2000.
Green et al., Systematic review of randomised controlled trials of interventions for painful shoulder: . . . , BMJ vol. 316 pp. 354-359, Jan. 31, 1998.
Gybeis et al., The Treatment of Pain Due to Peripheral Nerve Injury by Electrical Stimulation of the Injured Nerve, Advances in Pain Research & Therapy, vol. 13, 217-222, 1990.
Griffin et al., Strapping the hemiplegic shoulder prevents development of pain during rehabilitation: a randomized controlled trial, Clinical Rehabil, 20, 287-295, 2006.
Gustafsson et al., A programme of static positional stretches does not reduce hemiplegic shoulder pain or maintain . . . , Clinical Rehabil, 20, 277-286, 2006.
Hanger et al., A randomized controlled trial of strapping to prevent post-stroke shoulder pain, Clinical Rehabil, 14, pp. 370-380, 2000.
Hurd et al., Shoulder Sling for Hemiplegia: Friend or Foe?, Arch Phys Med Rehabil, vol. 55, pp. 519-522, Nov. 1974.
Kilgore et al., Synthesis of Hand Grasp Using Functional Neuromuscular Stimulation, IEEE Trans Biomed Eng, 36(7), pp. 761-770, Jul. 1989.
Krainick et al., Pain reduction in amputees by long-term spinal cord stimulation, J Neurosurg, 52, pp. 346-350, 1980.
Krainick et al, Spinal Cord Stimulation in Postamputation Pain, Surg Neurol, 4 (1), pp. 167-170, Jul. 1975.
Knutson et al., Electrode fracture rates and occurrences of infection and granuloma associated with precutaneous . . . J of Rehab Res Dev, vol. 39, No. 6, pp. 671-634, Nov./Dec. 2002.
Lindgren et al, Shoulder Pain After Stroke A Prospective Population-Based Study, Stroke, pp. 343-348, Feb. 2007.
Loeb et al., The BION devices: injectable interfaces with preipheral nerves and muscles, Neurosurg Focus, 20(5):E2, pp. 1-9, 2006.
Loeser MD, The Future Will pain be abolished or just pain specialists?, Minnesota Medicine, pp. 20-21, Jul. 2001.
Long MD, Electrical stimulation for relief of pain from chronic nerve injury, J Neurosurg, vol. 39, pp. 718-722, Dec. 1973.
Lynch et al, Continuous passive motion improves shoulder joint integrity following stroke, Clinical Rehabilitaiton, 19, pp. 594-599, 2005.
Melzack et al., On the Nature of Cutaneous Sensory Mechanisms, Brain, 85, pp. 331-356, Jun. 1962.
Melzack et al., Pain Mechanisms: A New Theory, Science, vol. 150, No. 3699, pp. 971-979, Nov. 19, 1965.
Memberg et al, An Analysis of the Reliability of Percutaneous Intramuscular Electrodes in Upper Extremith FNS Appl.., IEEE Trans Rehabil Eng, vol. 1, No. 2, 126-132, Jun. 1993.
Moe et al., Functional Electrical Stimulation for Ambulation in Hemiplegia, The Journal Lancet, pp. 285-288, Jul. 1962.
Mortimer et al., Intramuscular Electrical Stimulation: Tissue Damage, Annals Biomed Eng, vol. 8, pp. 235-244, 1980.
Nashold et al., Peripheral nerve stimulation for pain relief using a multicontact electrode system, J Neurosurg, 51, pp. 872-873, 1979.
Nashold et al., Electrical stimulation of peripheral nerves for relief of intractable chronic pain, Medical Instrumentation, vol. 9, No. 5, pp. 224-225, Sep./Oct. 1975.
Nashold et al., Long-term pain control by direct peripheral-nerve stimulation, The Journal of Bone and Joint Surgery, vol. 64-A, No. 1, pp. 1-10, Jan. 1982.
R North, Spinal cord and peripheral nerve stimulation: technical aspects, Pain Research and Clinical Management, Elsevier, vol. 15 (Ch 12), pp. 183-195, 2003.

(56) References Cited

OTHER PUBLICATIONS

North et al, Spinal cord stimulation for chronic, intractable pain: superiority of "multi-channel" devices, Pain 44, pp. 119-130, 1991.
Picaza et al., Pain Suppression by Pheripheral Nerve Stimulation Part II Observations with Implanted Devices, Surg Neurol, vol. 4, pp. 115-126, Jul. 1975.
Picaza et al., Pain Suppression by Pheripheral Nerve Stimulation Part I Observations with Transcutaneous Stimuli, Surg Neural, vol. 4, pp. 105-114, Jul. 1975.
Picaza et al., Pain Suppression by Pheripheral Nerve Stimulation Chronic Effects of Implanted Devices, Appl Neurophysiol, 40, pp. 223-234, 1977/78.
Poulin de Courval et al., Painful shoulder in the hemilegic and unilateral neglect, Arch Phys Med Rehabil, vol. 71, pp. 673-676, Aug. 1990.
D J Price, The shoulder block: a new alternative to interscalene brachial plexus blockade for the control of postoperative shoulder pain, Anaesth Inten Care, 35, 575-531, 2007.
Rajaram et al., Shoulder forearm support for the subluxed shoulder, Arch Phys Med Rehabil, vol. 66, pp. 191-192, Mar. 1985.
Renzenbrink et al., Percutaneous neuromuscular electrical stimulation (P-NMES) for treating shoulder pain in chronic hemiplegia . . . Clinical Rehabil, 18, 359-365, 2004.
Ratnasabapathy et al., Shoulder pain in people with a stroke: a population-based study, Clinical Rehabil, 17, 304-311, 2003.
Sator-Katzenschlager et al., Subcutaneous Target Stimulation (STS) in chronic noncancer pain . . . , Pain Practice, vol. 10, Issue 4, 279-286, 2010.
Sharan et al., Evolving patterns of spinal cord stimulation in patients implanted with intractable low back and leg pain, Neuromodulation. vol. 5, No. 3, 167-179, 2002.
Sheffler et al., Neuromuscular electrical stimulation in neurorehabilitation, Muscle and Nerve, pp. 562-590, May 2007.
Snels et al., Effect of triamcinolone acetonide injections on hemiplegic shoulder pain A randomized clinical trial, Stroke, 2396-2401, Oct. 2000.
Snels et al.. Treatment of hemiplegic shoulder pain in the Netherlands: results of a national survey, Clinical Rehabilitation, 14, 20-27, 2000.
Spincemaille et al, Technical data and complications of spinal cord stimulation: data from a randomized trial on critical limb . . . , Stereotact Funct Neurosurd 74, 63-72, 2000.
Teasell et al., Evidence-based review of stroke rehabilitation Appendix: Management of Post Stroke Pain, 10th Ed, 1-37, 2003.
Turner-Stokes et al., Shoulder pain after stroke: a review of the evidence base to inform the development of an integrated care pathway, Clinical Rehabil, 16, 276-298, 2002.
Van Ouwenalle et al., Painful shoulder in hemiplegia, Arch Phys Med Rehabil, vol. 67, 23-26, Jan. 1986.
Van der Windt et al., Review the efficacy of non-steroidal anti-inflammatory drugs (NSAIDS) for shoulder complaints . . . , J Clin Epidermiol, vol. 48, no. 5, 691-704, 1995.
J J Wall MD, Axillary Nerve Blocks, Am Fam Physician, vol. 11, No. 5, 135-142, May 1975.
Wanklyn et al., Hemiplegic shoulder pain (HSP): natural history and investigation of associated features, Disability and Rehabil, vol. 18, No. 10, 497-501, 1996.
Ware et al., The MOS 36-Item Short-Form Health Survey (SF-36) I Conceptual Framework and Item Selection, Medical Care, vol. 30 No. 6, 473-483, Jun. 1992.
Wider et al., Heaith-related quality of life in persons with long-term pain after a stroke. J of Clinical Nursing, 13, 497-505, 2004.
Yu et al., Muscular Factors preventing inferior subluxation of the shoulder in hemiplegia, Arch Phys Med Rehabil, vol. 79, Sep. 1998.
Yu et al., Comparing stimulation-induced pain during percutaneous (Intramuscular) and transcutaneous neuromuscuiar . . . Arch Phys Med Rehabil, vol. 82, 756-760, Jun. 2001.
Yu et al., Percutaneous intramuscular neuromuscular electric stimulation for the treatment of shoulder subluxation and pain . . . , Arch Phys Med Rehabil, vol. 82, 20-25, Jan. 2001.
Yu et al, Case Report A Neuroprosthesis for high tetraplegia, The J of Spinal Cord Medicine, vol. 24, No. 2, 109-113, Summer 2001.
Yu et al,, Intramuscular neuromuscular electric stimulation for poststroke shoulder pain: A Multicenter randomized . . . , Arch Phys Med Rehabil, vol. 85 695-704, May 2004.
Zorowitz et al., Shoulder Pain and Subiuxation after stroke: Correlation or Coincidence?, The American Journal of Occupational Therapy, vol. 50, No. 3, 194-201, Mar. 1996.
Office Action dated Mar. 16, 2005 in U.S. Appl. No. 09/862,156.
Office Action dated Jul. 12, 2004 in U.S. Appl. No. 09/862,156.
Office Action dated Oct. 29, 2003 in U.S. Appl. No. 09/862,156.
Office Action dated Feb. 18, 2003 in U.S. Appl. No. 09/862,156.
Notice of Allowance mailed Feb. 21, 2003 in U.S. Appl. No. 10/138,791.
Notice of Allowability mailed Jul. 22, 2003 in U.S. Appl. No. 10/138,791.
Office Action dated May 4, 2007 in U.S. Appl. No. 10/867,396.
Office Action dated Dec. 1, 2010 in U.S. Appl. No. 11/982,789.
Office Action dated May 28, 2010 in U.S. Appl. No. 11/982,789.

* cited by examiner

SYSTEMS AND METHODS TO PLACE ONE OR MORE LEADS IN MUSCLE FOR PROVIDING ELECTRICAL STIMULATION TO TREAT PAIN

RELATED APPLICATIONS

This application claims the benefit of U.S. Provisional Patent Application Ser. No. 61/137,652, filed 1 Aug. 2008, and entitled "Portable Assemblies, Systems, and Methods for Providing Functional or Therapeutic Neurostimulation."

This application also claims the benefit of U.S. Provisional patent application Ser. No. 61/201,116, filed 5 Dec. 2008, and entitled "Systems and Methods to Place One or More Leads in Tissue for Providing Functional and/or Therapeutic Stimulation."

This application is also a continuation-in-part of U.S. patent application Ser. No. 11/982,789, filed 5 Nov. 2007 now U.S. Pat. No. 8,249,713, and entitled "Treatment of Shoulder Dysfunction using a Percutaneous Intramuscular Stimulation System," which is a continuation of U.S. patent application Ser. No. 10/867,396, filed 14 Jun. 2004, now abandoned, which is a divisional of U.S. patent application Ser. No. 10/138,791, now U.S. Patent No. 6,845,271, filed 3 May 2002, which is a continuation-in-part of U.S. patent application Ser. No. 09/862,156, filed 21 May 2001, now abandoned, which is a continuation of U.S. patent application Ser. No. 09/089,994 filed 3 June 1998, now abandoned, all of the above which are incorporated herein by reference.

FIELD OF INVENTION

This invention relates to systems and methods for percutaneously placing one or more leads in muscle for providing electrical stimulation to a motor point(s) in the muscle to treat the perception of pain.

BACKGROUND OF THE INVENTION

The electrical stimulation of nerves, often afferent nerves, to indirectly affect the stability or performance of a physiological system can provide functional and/or therapeutic outcomes, and has been used for activating target nerves to provide therapeutic relief of pain.

While existing systems and methods have been shown to provide remarkable benefits to individuals requiring therapeutic relief, many issues and the need for improvements still remain.

Many techniques have been developed to treat pain, but all of them are ultimately insufficient.

Non-narcotic analgesics, such as acetaminophen or non-steroidal anti-inflammatory drugs (NSAIDS), have relatively minor side effects and are commonly used for several types of pain. However, they are rarely sufficient in managing moderate to severe chronic pain (Sherman et al. 1980; Loeser 2001a; Rosenquist and Haider 2008).

The use of narcotic analgesics, such as N-methyl-D-aspartate (NDMA) antagonists, has shown only minor success with inconsistent results. Narcotics carry the risk of addiction and side effects, such as nausea, confusion, vomiting, hallucinations, drowsiness, dizziness, headache, agitation, and insomnia.

Psychological strategies, such as biofeedback and psychotherapy, may be used as an adjunct to other therapies but are seldom sufficient, and there are few studies demonstrating efficacy.

Electrical stimulation systems have been used for the relief of pain, but widespread use of available systems is limited.

There exist both external and implantable devices for providing electrical stimulation to activate nerves and/or muscles to provide therapeutic relief of pain. These "neurostimulators" are able to provide treatment and/or therapy to individual portions of the body. The operation of these devices typically includes the use of one or more electrodes placed either on the external surface of the skin and/or a surgically implanted electrode. In most cases, surface electrode(s), cuff-style electrode(s), paddle-style electrode(s), spinal column electrodes, and/or percutaneous lead(s) having one or more electrodes may be used to deliver electrical stimulation to the select portion of the patient's body.

Transcutaneous electrical nerve stimulation (TENS) has been cleared by the FDA for treatment of pain. TENS systems are external neurostimulation devices that use electrodes placed on the skin surface to activate target nerves below the skin surface. TENS has a low rate of serious complications, but it also has a relatively low (i.e., less than 25%) long-term rate of success.

Application of TENS has been used to treat pain successfully, but it has low long-term patient compliance, because it may cause additional discomfort by generating cutaneous pain signals due to the electrical stimulation being applied through the skin, and the overall system is bulky, cumbersome, and not suited for long-term use (Nashold and Goldner 1975; Sherman 1980; Finsen et al. 1988).

In addition, several clinical and technical issues associated with surface electrical stimulation have prevented it from becoming a widely accepted treatment method. First, stimulation of cutaneous pain receptors cannot be avoided resulting in stimulation-induced pain that limits patient tolerance and compliance. Second, electrical stimulation is delivered at a relatively high frequency to prevent stimulation-induced pain, which leads to early onset of muscle fatigue in turn preventing patients from properly using their arm. Third, it is difficult to stimulate deep nerves and/or muscles with surface electrodes without stimulating overlying, more superficial nerves and/or muscles resulting in unwanted stimulation. Finally, clinical skill and intensive patient training is required to place surface electrodes reliably on a daily basis and adjust stimulation parameters to provide optimal treatment. The required daily maintenance and adjustment of a surface electrical stimulation system is a major burden on both patient and caregiver.

Spinal cord stimulation (SCS) systems are FDA approved as implantable neurostimulation devices marketed in the United States for treatment of pain. Similar to TENS, when SCS evokes paresthesias (generally described as a comfortable tingling sensation) that cover the region of pain, it confirms that the location of the electrode and the stimulus intensity should be sufficient to provide pain relief and pain relief can be excellent initially, but maintaining sufficient paresthesia coverage is often a problem as the lead migrates along the spinal canal (Krainick et al. 1980; Sharan et al. 2002; Buchser and Thomson 2003).

Spinal cord stimulation is limited by the invasive procedure and the decrease in efficacy as the lead migrates. When it can produce paresthesias in the region of pain, spinal cord stimulation is typically successful initially in reducing pain, but over time the paresthesia coverage and pain reduction is often lost as the lead migrates away from its target (North et al. 1991; Andersen 1997; Loeser 2001a).

Lead migration is the most common complication for spinal cord stimulators occurring in up to 45-88% of the cases (North et al. 1991; Andersen 1997; Spincemaille et al. 2000;

Sharan et al. 2002). When the lead migrates, the active contact moves farther from the target fibers and loses the ability to generate paresthesias in the target area. SCS systems attempt to address this problem by using leads with multiple contacts so that as the lead travels, the next contact in line can be selected to be the active contact.

Peripheral nerve stimulation may be effective in reducing pain, but it previously required specialized surgeons to place cuff- or paddle-style leads in intimate contact with or around the nerves in a time consuming procedure.

Percutaneous, intramuscular electrical stimulation for the treatment of post-stroke shoulder pain has been studied as an alternative to surface electrical stimulation. A feasibility study (Chae, Yu, and Walker, 2001) and a pilot study (Chae, Yu, and Walker, 2005) showed significant reduction in pain and no significant adverse events when using percutaneous, intramuscular electrical stimulation in shoulder muscles.

While the above mentioned percutaneous electrical stimulation system overcame some of the barriers of surface electrical stimulation, it faced some additional drawbacks having to deal with the placement of multiple leads in different muscle locations, and then the containment of these multiple leads during use of the stimulation system.

As previously described, electrical stimulation has been used and shown to be effective in treating pain, but present methods of implementation have practical limitations that prevent widespread use. External systems are too cumbersome, and implanted spinal cord stimulation systems require complex implantation techniques, and often have problems of lead migration along the spinal canal, resulting in either the need for frequent reprogramming or clinical failure. Peripheral nerve stimulation requires specialized surgeons to place cuff- or paddle-style leads in intimate contact with or around the nerves in a time consuming procedure.

It is time that systems and methods for providing electrical stimulation address not only specific therapeutic objectives, but also address and improve the quality of life of the individual requiring the therapy, including a need to treat pain with minimally-invasive systems and methods that include intramuscular lead(s) that can be inserted percutaneously into muscle near a motor point(s), may not require reprogramming and/or repositioning, and are better adapted to resist migration within the muscle.

SUMMARY OF THE INVENTION

The invention provides systems and methods for percutaneously placing one or more intramuscular (IM) leads in muscle for providing electrical stimulation to a motor point(s) in the muscle to treat the perception of pain.

One aspect of the invention places one or more leads in a muscle to activate one or more motor points innervating the muscle in a system for the relief of pain. The systems and methods optimally allow using a single lead, although it is to be appreciated that more than one lead(s) may be used, to activate one or more motor points innervating the muscle.

Another aspect of the invention provides systems and methods including lead placement procedures that may be used for placing a single lead to activate more than one motor point simultaneously, i.e., a motor point innervating a muscle A and a motor point innervating a muscle B simultaneously, (e.g., the middle and posterior deltoid muscle) in a system for the relief of shoulder pain, but is not exclusive to this application. The procedures optimally allow using only a single lead, although it is to be appreciated that more than one lead(s) may be used, to activate two motor points of adjacent muscles optimally.

Yet another aspect of the invention comprises a method to reduce and/or relieve pain. The method includes percutaneously placing an intramuscular lead into a muscle in a region where pain is felt, such that the lead is in electrical proximity, but not touching, a motor point within the muscle, and electrically stimulating the motor point within the muscle where the lead is placed to reduce and/or relieve the pain in the region where the pain is felt. The intramuscular lead may include at least one anchoring member to anchor the lead in the muscle. Electrically stimulating the motor point may reduce and/or relieve the pain without any functional movement or response. The region where the pain is felt may include the muscle where the intramuscular lead is placed.

Another aspect of the invention comprises a method to alleviate pain. The method includes identifying a tissue region where pain is perceived including skeletal muscle innervated by a peripheral nerve and including a motor point, placing at least one intramuscular lead having at least one electrode within the skeletal muscle in electrical proximity, but not touching, the motor point, and applying therapeutic electrical stimulation to the at least one electrode according to predefined therapeutic electrical stimulation parameters to affect afferent and/or efferent nerve stimulation within the skeletal muscle and to provide the therapeutic electrical stimulation to the motor point to alleviate pain without any functional nerve stimulation involving the skeletal muscle.

In one embodiment, the step of identifying the tissue region may include locating the motor point by percutaneously placing a first lead and applying the therapeutic electrical stimulation to the first lead and adjusting the position of the first lead until a muscle twitch is observed in the skeletal muscle. The motor point may be located without any feedback from the patient.

In an additional aspect of the invention comprises a method of therapeutically stimulating a motor point of a peripheral nerve to reduce the perception of pain in a muscle region innervated by the peripheral nerve, without stimulating the motor point to produce a functional response. The method includes percutaneously placing at least one intramuscular lead having at least one electrode in the muscle region where the perception of pain is experienced, and electrically stimulating the motor point with the at least one electrode to reduce the perception of pain in the muscle region. Electrically stimulating the motor point may require evoking a muscle contraction in the muscle to confirm correct lead placement. The steps to place the IM lead percutaneously near the motor point and to evoke a muscle contraction may be accomplished between about one minute and about thirty minutes.

An additional aspect of the invention comprises a method of placing a first lead in electrical proximity to a first motor point of a first muscle, placing a second lead in electrical proximity to a second motor point of a second muscle, placing a third lead in electrical proximity to a point generally in-between the first lead in electrical proximity to the first motor point of the first muscle and the second lead in electrical proximity to the second motor point of the second muscle, and providing electrical stimulation to the third lead to activate the motor point of the first muscle and the motor point of the second muscle. The first muscle and the second muscle may be activated simultaneously, and the first lead and the second lead may be a different configuration than the third lead. For example, the third lead may be an intramuscular lead and the first lead and the second lead may be EMG leads.

In one embodiment, the method may include recording electrical stimulation parameters used to activate the motor point of the first muscle and/or the motor point of the second muscle. In another embodiment, the method may include recording electrical stimulation parameters provided to the third lead to activate the motor point of the first muscle and the motor point of the second muscle. The first muscle may comprise the middle deltoid muscle, and the second muscle may comprise the posterior deltoid muscle, and the electrical stimulation applied to the third lead provides relief of shoulder pain. The method may include removing the first lead and the second lead after placing the third lead. The electrical stimulation applied to the third lead desireably provides relief of pain to both the first muscle and the second muscle.

Another aspect of the invention provides systems and methods for providing therapeutic electrical stimulation to a muscle region where pain is felt to reduce the perception of pain in a muscle region. A system may comprise an intramuscular lead having at least one electrode, the lead and electrode adapted to be placed between motor points of at least two muscles, and a pulse generator adapted to provide the therapeutic electrical stimulation to the lead and electrode to therapeutically stimulate the motor points of the at least two muscles to reduce the perception of pain in the muscle region. In one embodiment, the intramuscular lead includes at least one anchoring member to anchor the lead in the muscle. The muscle region where pain is felt may comprise the at least two muscle where the intramuscular lead is placed.

Yet an additional aspect of the invention provides a system for providing therapeutic electrical stimulation to a region of pain to reduce the perception of pain. The system may comprise an intramuscular lead having at least one electrode, the lead and electrode adapted to be placed in electrical proximity but not touching a motor point of a muscle, and a pulse generator adapted to provide the therapeutic electrical stimulation to the lead and electrode to therapeutically stimulate the motor point of the muscle to reduce the perception of pain in the region of pain. In one embodiment, the pulse generator may be adapted to provide the therapeutic electrical stimulation to the lead and electrode to therapeutically stimulate the motor point of the muscle to reduce the perception of pain in the muscle without the generation of paresthesias, although some paresthesias may be perceived.

In one embodiment, the therapeutic electrical stimulation is adapted to provide a therapeutic stimulation function, the therapeutic stimulation function including a function selected from a group comprising the treatment of (i) shoulder pain, (ii) arm pain, (iii) calf pain, (iv) leg pain, (v) neck pain, (vi) head pain, and (vii) back pain.

Yet an additional aspect of the invention provides systems and methods, including a method of reducing the perception of pain in a muscle region, the method comprising placing an intramuscular lead in muscle near but not touching a motor point of the muscle, providing therapeutic electrical stimulation via the intramuscular lead to the motor point of the muscle, activating the motor point of the muscle with the therapeutic electrical stimulation, and causing the reduction of the perception of pain in the muscle region where the lead is placed. The intramuscular lead may be placed percutaneously via an introducer. The therapeutic electrical stimulation may be applied without causing the generation of paresthesias, although some paresthesias may be perceived. The muscle region where the pain is perceived may comprise the muscle where the intramuscular lead is placed.

The therapeutic electrical stimulation may be applied to target motor points in muscles, the muscles comprising the posterior, anterior, and/or middle dletoid, trapezius, erector spinae, gastrocnemius, occipitailis, gluteus maximus, gluteus medius, iliotibial band, biceps femoris, adductor magnus, semitendinosus, gracilis, semimembranosus, sartorius, pectineus, adductor longus, vastus medialis, vastus lateralis, and rectus femoris, as non-limiting examples.

Other features and advantages of the inventions are set forth in the following specification and attached drawings.

DESCRIPTION OF THE PREFERRED EMBODIMENT

Figure 1A:
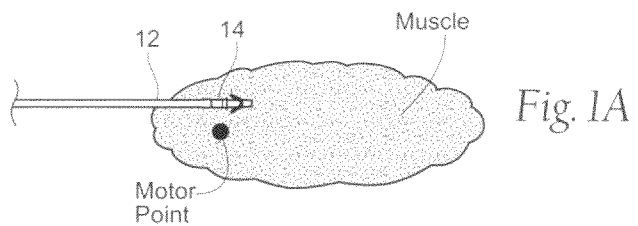
FIGS. 1A through 1C are schematic diagrams showing placement of one or more intramuscular leads to stimulate one or more motor points.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Any elements described herein as singular can be pluralized (i.e., anything described as "one" or "a" can be more than one), and pluralized elements may be singular. Any species element of a genus element can have the characteristics or elements of any other species element of that genus. The described configurations, elements or complete assemblies and methods and their elements for carrying out the invention, and variations of aspects of the invention can be combined and modified with each other in any combination.

The various aspects of the invention will be described in connection with the placement of one or more intramuscular leads 12 having one or more electrodes 14, in muscle, and in electrical proximity to, but not in intimate contact with, motor points and/or nerves, for improved recruitment of targeted nerves for therapeutic purposes, such as for the treatment of pain, including but not limited to shoulder pain, arm pain, calf pain (e.g., claudication pain), leg pain, neck pain, head pain (e.g., migraine), and back pain (e.g., pain related to failed back surgery syndrome) as non-limiting examples. That is because the features and advantages that arise due to the invention are well suited to this purpose. Still, it should be appreciated that the various aspects of the invention can be applied to achieve other objectives as well, and that any known motor point(s) may be stimulated in accordance with the invention for the therapeutic purpose of the treatment of pain.

I. Reduction of Pain

The present novel invention provides systems and methods for the reduction of pain. The systems and methods of the present invention are adapted to reduce pain by stimulating a motor point, and/or a target nerve, of a muscle, i.e., the motor point and/or nerve that innervate the muscle where the region(s) of pain are felt. A motor point is known to be a region on or in a muscle where the application of an electrical stimulation will cause the contraction of the muscle. It is to be appreciated that regions of pain can include any or all portions of the body, including arms, legs, head, neck, and torso in both humans and animals.

Motor point stimulation can also be described as essentially muscle stimulation, wherein an IM lead is placed near the target motor point in the target muscle innervated by the target nerve to relieve pain in the region of pain, which may include the target muscle. The target muscle is desirably the same muscle in which the lead is placed. As one non-limiting example, an IM lead may be placed near the motor points of the deltoid muscle to relieve pain in the deltoid muscle, i.e., the pain is felt and relieved in the area where the IM lead is located. Placement of the lead(s) "near" or "near but away from" or "in electrical proximity to" or "not touching" the motor point(s) can include, but are not limited to, one or more lead diameter lengths away from the motor point(s), although it is to be appreciated that the lead(s) may be closer in some applications and farther away in other applications. The lead is desirably close enough to the motor point to cause muscle contraction without inducing additional discomfort or pain. It is to be appreciated that a stimulus intensity high enough to cause muscle contraction may be beneficial to aid in the placement of the lead(s), but may not be required for the therapeutic purpose of the treatment of pain. For example, a sub-threshold stimulus intensity (e.g., where no muscle contraction is caused), may be sufficient for the therapeutic purpose of the treatment of pain.

There is familiarity with motor point stimulation by physiatrists who are used to placing needles superficially near motor points, typically in EMG needle placement and nerve conduction studies, and physiatrists are accustomed to using motor responses to guide needle placement.

Some motor points, but not all, are located relatively superficially. This allows for systems and methods where imaging, such as fluoroscopy or ultrasound, are not required to place the IM lead for motor point stimulation, although either may be used.

Motor point stimulation may require evoking a muscle contraction to confirm correct lead placement, but does not require generation of paresthesias (although possible) or patient feedback of sensation to locate the lead correctly. The muscle that contracts is the same muscle in which the IM lead is placed, and may be where the region(s) of pain are felt.

The patient is not required to give verbal, written, or other type of feedback or indication of what they feel as the IM lead is being advanced towards the motor point. This minimizes patient involvement and simplifies the procedure for the clinician.

After the IM lead has been correctly positioned, the patient may indicate sensations during tuning of stimulus intensity. As non-limiting examples, those sensations reported by the patient may include first sensation (minimum stimulus intensity that evokes a sensation), level of comfort, maximum tolerable sensation, pain, and/or qualities and/or descriptions of the sensations.

The primary targeted pain area may be, but does not need to be, proximal to the IM lead. For example, in the case of shoulder pain, the lead may be placed distal to (or more peripheral than) the shoulder, meaning that the area of shoulder pain is in between the IM lead and the center of the body (e.g., the spinal cord).

Use of the intramuscular lead is intended to relieve pain by modulating and/or changing one or more sensations, which is known as therapeutic electrical stimulation. This is in stark contrast from previous uses of an IM lead intended to achieve functional movement or response (utility), which is known as functional electrical stimulation or FES. Muscle contraction is not to be considered a functional movement or response.

Placement of an intramuscular lead in electrical proximity to, but not touching, a motor point is primarily for the purpose of evoking muscle contraction and is primarily to simplify the lead placement procedure and to confirm that the stimulus intensity is sufficient without needing more complicated sensory feedback from the patient. The combination of the IM lead and the desired placement makes the systems and methods simpler and also more robust than prior systems intended to treat pain. Even if the lead migrates, as long as stimulation is evoking muscle contraction, the clinician and patient know that the lead is still sufficiently close to the motor point and that the stimulus intensity is sufficiently high.

The muscle contraction(s) confirms that the stimulus intensity is above a threshold, i.e., is high enough, to activate the larger A fibers that can "close the gate" and prevent activity in the smaller C fibers that transmit nociceptive information from reaching higher centers in the central nervous system and keep the patient from feeling the pain. In other words, seeing the muscle twitch is an indicator that stimulus intensity is sufficient to provide pain relief.

The muscle contraction(s) may also indirectly generate additional activation of afferent fibers by contracting the muscle. For example, one set of afferents in the target nerve may be directly activated by electrical stimulation, e.g., at a location near the electrode. Action potentials in these afferent fibers may be generated by the electrical signals coming directly from the electrode contact. If the stimulating frequency is 12 Hz (for example), then these afferent fibers are being excited and firing at 12 Hz. There should be approximately a one-to-one ratio between the stimulating frequency and the rate of afferent action potentials. Firing of these afferents due to the electrical stimulation may be more or less synchronized.

Another set of afferents that innervate the muscle, such as those that respond to and "sense" muscle contraction, may be activated by the muscle contraction, which happened to be evoked by electrical stimulation of the motor point. These afferents would be similarly activated if the person chose to repeatedly flex or contract their muscle, i.e., without electrical stimulation. This secondary or indirect activation of afferents may be more natural and/or desynchronized, and may increase the potential therapeutic effect of pain relief.

Action potentials in the afferent fibers are generated by physical signals, e.g., pressure, stretch, movement, etc., due to muscle contraction. The stimulating frequency may not correspond to the frequency with which action potentials are generated in the afferent fibers. There may likely be a distribution of the frequencies at which the afferent fibers are propagating the action potentials. Firing of the afferent fibers, due to muscle contraction, may likely be somewhat desynchronized, similar to what would be expected during voluntary muscle contraction.

These two sets of afferents may or may not include some or all of the same afferents. Since activation of afferents via electrical stimulation and/or muscle contraction may be able to provide pain relief, the systems and methods of the present invention take advantage of both, and the combined effect of the direct and indirect activation of afferents may enhance the ability to treat the pain.

The present novel invention provides systems and methods that place percutaneous IM lead(s) 12 appropriately in muscle to electrically activate a motor point(s) of nerve(s) that carry the pain signal(s). For example, if there is pain in the deltoid region, e.g., shoulder, the systems and methods are well adapted to stimulate the motor points of the deltoid muscles. If electrical stimulation activates the motor points sufficiently at an acceptable intensity, the pain signal will be reduced. As previously described, the patient may also feel, but is not required to feel, the comfortable tingling sensation called a paresthesia in the same region as their pain. It is to be appreciated that the sensation could be described with other words such as buzzing, thumping, etc. Just as the patient can have pain in a specific body region, electrical stimulation can evoke paresthesias that the patient also feels in the specific body region. It is not necessary to evoke paresthesias in the regions of pain to confirm correct IM lead placement, and it is possible that pain relief may be achieved without the patient reporting any sensation of electrically evoked paresthesias.

Figure 1B:
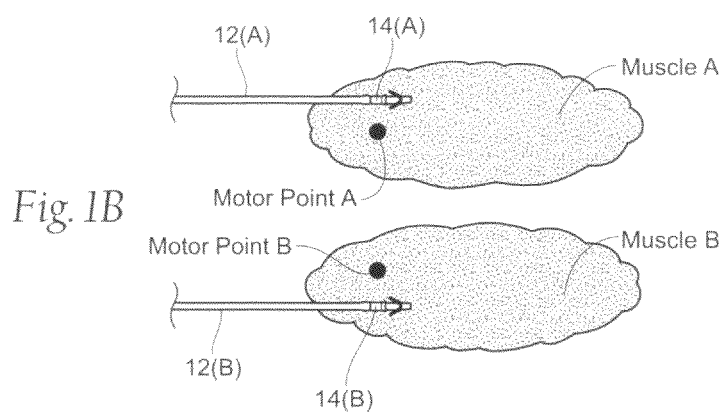
Figure 1C:
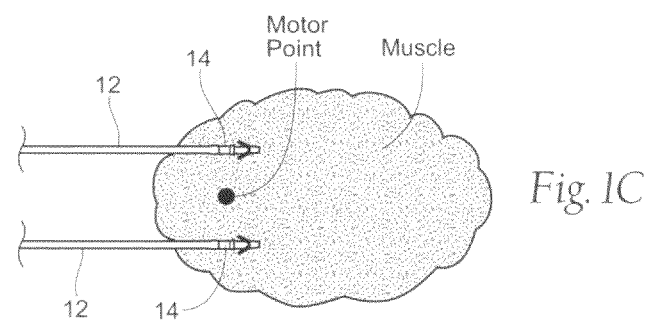
Figure 2:
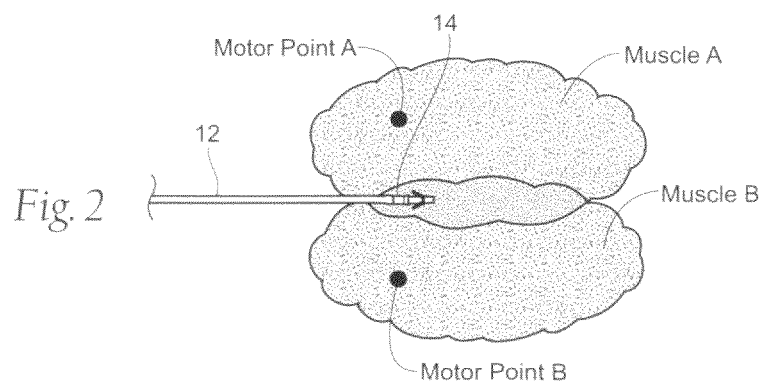
FIG. 2 is a schematic diagram similar to FIGS. 1A through 1C, showing placement of a single intramuscular lead to stimulate more than one motor point simultaneously.

As shown in FIGS. 1A through 2, the systems and methods are well adapted to activate the motor point of a muscle by placing a lead 12 with its electrode 14 close, i.e., in electrical proximity but not touching, to the motor point (see FIG. 1A). FIG. 1B shows the use of two leads 12(A) and 12(B), to stimulate motor points in muscle A and muscle B, respectively. FIG. 1C shows the use of more than one lead 12, e.g., two leads, to stimulate the motor point of a muscle. FIG. 2 shows the use of one lead 12 to stimulate the motor point A of muscle A and the motor point B of muscle B. It is to be appreciated that the intramuscular leads 12 may incorporate a single electrode 14, or may incorporate more than one electrode, e.g., four or eight electrodes, as a non-limiting example.

As previously described, a motor point can be defined as the location where the innervating nerve enters the muscle. At that location, the electrical stimulation intensity required to elicit a full contraction is at the minimum. Any other location in the muscle would require more stimulation intensity to elicit the same muscle contraction.

Figure 3A:
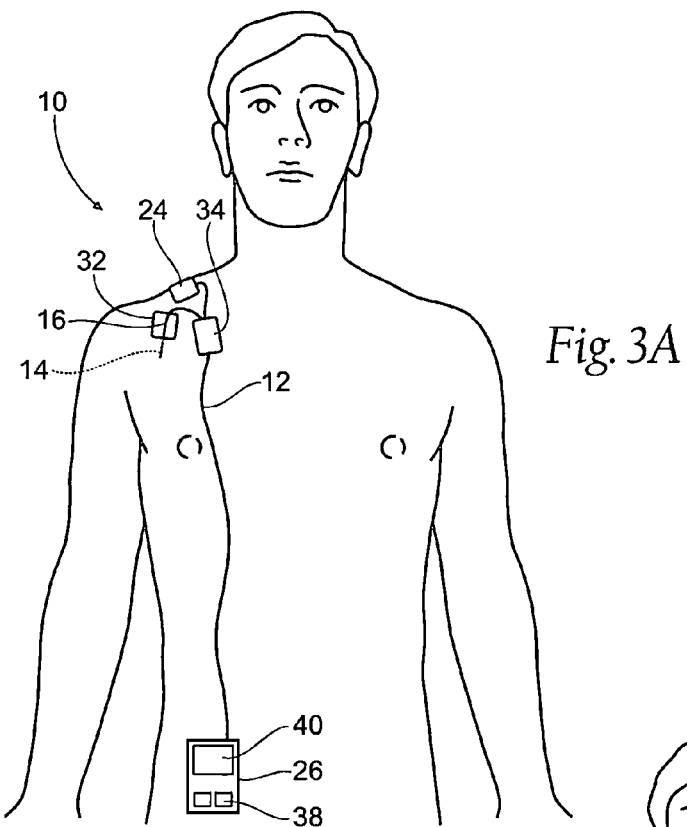
FIGS. 3A and 3B are anatomical views of a patient utilizing an embodiment of the present invention, including a percutaneous lead coupled to an external pulse generator or an implantable pulse generator.
Figure 3B:
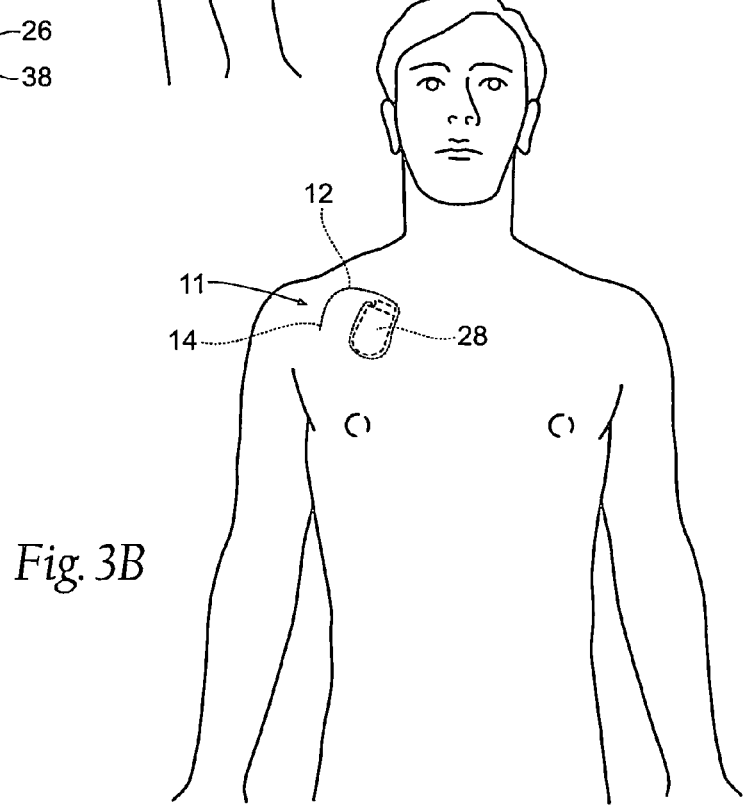
Figure 4A:
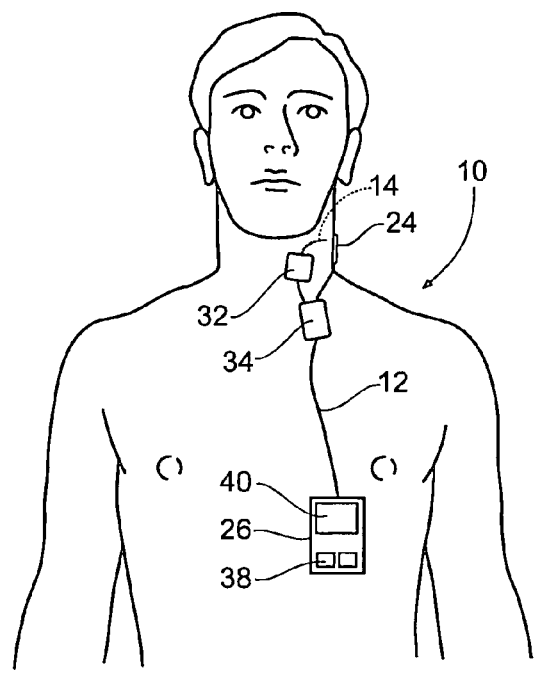
FIGS. 4A and 4B are anatomical views of patients utilizing an embodiment of the present invention to treat calf pain (FIG. 4A) and neck pain (FIG. 4B).
Figure 4B:
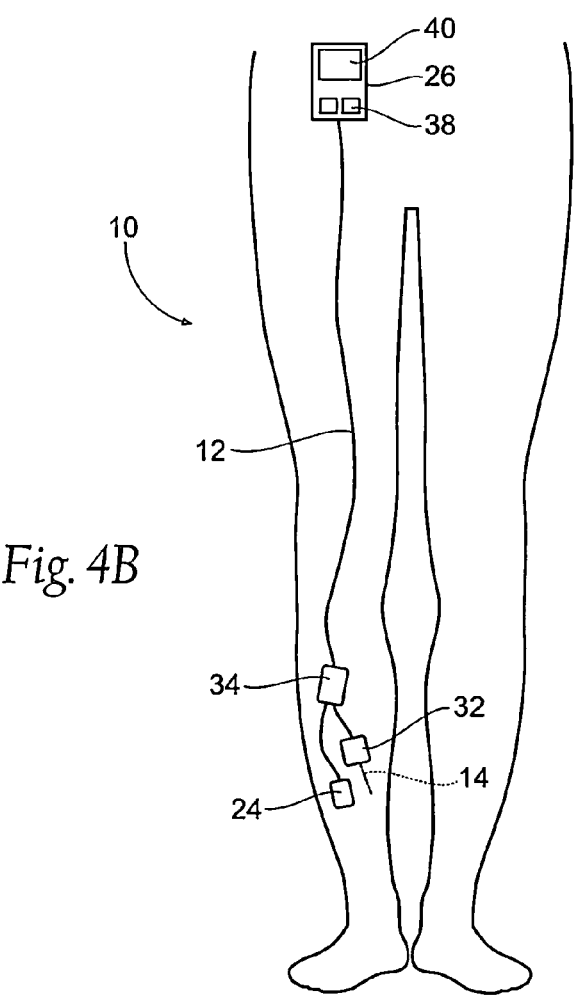
Figure 5:
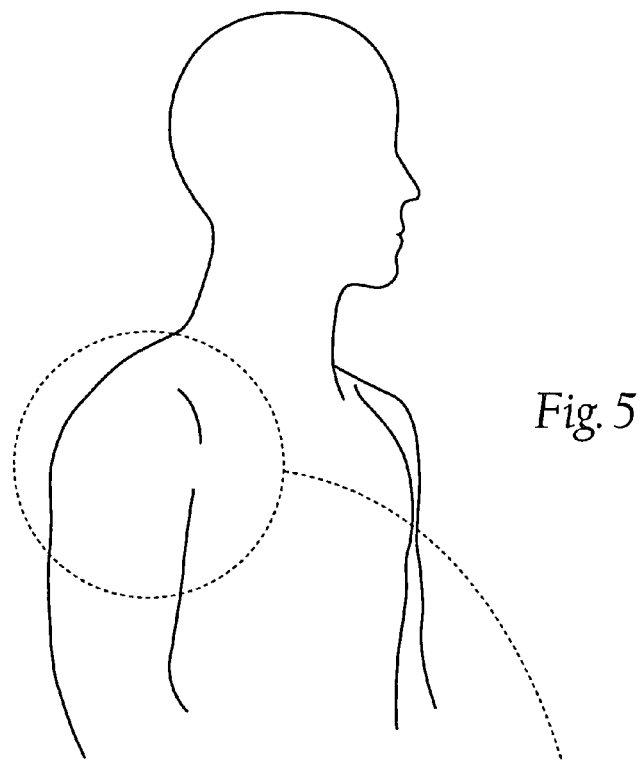
FIGS. 5 and 6 are anatomical views of a patient's shoulder showing the placement of a needle electrode placed in proximity to motor point A and a needle electrode placed in proximity to motor point B.
Figure 6:
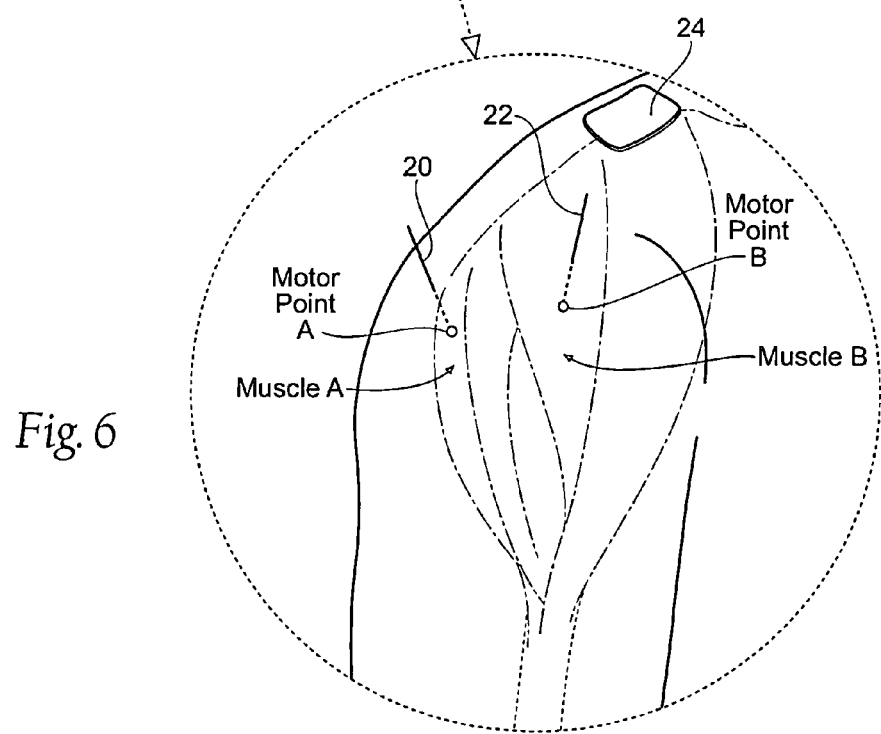

The ability to insert the IM lead 12 percutaneously near a motor point simplifies the approach to a quick (e.g., about 1 to about 5, or 10, or 20, or 30 minute, or more or less) procedure, such as an out-patient procedure that can be performed in a standard community-based clinic, allowing widespread use and providing a minimally-invasive screening test to determine if patients will benefit from the systems and methods of the present invention, including a percutaneous system 10 and/or a fully implanted system 11. FIGS. 3A and 3B show a percutaneous system 10 and a fully implanted system, respectively, to stimulate one or more motor points in the shoulder to relieve pain in the shoulder. FIG. 4A shows the use of a percutaneous system 10 to relieve pain in the neck region, and FIG. 4B shows the use of a percutaneous system 10 to relieve pain in the calf region.

The systems and methods of the present invention are well suited to place a percutaneous IM lead 12 near a motor point(s) with a quick procedure to generate electrically a therapeutic pulse train to reduce the patients' pain, without any functional stimulation or paresthesia.

In a percutaneous system 10, the lead 12 may be percutaneously placed near the motor point and exit at the skin puncture site 16 and coupled to an external pulse generator 26 (see FIG. 3A). The percutaneously placed IM lead 12 and external pulse generator 26 may provide a screening test function to confirm pain relief of the painful areas. If the screening test is successful, the patient may proceed to a home-trial (e.g., a day, week, month, or year, or more or less) to determine if pain relief can be sustained in the home environment. If either the screening test or home trial is unsuccessful, the IM lead 12 may be quickly and easily removed. It is to be appreciated that a home-trial is not a requirement for either the percutaneous system or a fully implanted system.

However, if the screening test and/or home-trial are successful, the patient's percutaneous system may be converted into a fully implanted system 11 by replacing the external pulse generator 26 with an implantable pulse generator 28 that is implanted in a convenient area (e.g., the subclavicular area), and coupling a new sterile lead 12, or a sterile lead extension, to the implantable pulse generator 28 (see FIG. 3B).

Inserting the lead 12 percutaneously allows the lead 12 to be placed quickly and easily, and placing the lead 12 in a peripheral location, i.e., muscle, where it is less likely to be dislodged, addresses the lead migration problems of spinal cord stimulation systems that result in decreased pain relief, and the need for frequent patient visits for reprogramming, and even lead repositioning.

In an exemplary embodiment of the present invention, placing the percutaneous IM lead 12 in muscle near the motor point minimizes complications related to lead placement and movement.

In the percutaneous system 10, the IM lead 12, such as a coiled fine wire IM lead may be used because it is minimally-invasive and previous studies suggest it will perform well in this location, i.e., in muscle, during use.

In the fully implanted system 11, the same or different lead 12 may be used, such as a slightly larger IM lead that may be sized and configured to withstand greater mechanical forces and resist migration during long-term use. A larger IM lead 12 may be sized and configured to withstand forces in excess of those anticipated in flexible regions of the body, such as the shoulder, elbow, neck, and knee.

II. Representative Indication for Temporary or Chronic Reduction of Pain

Localized pain in any area of the body can be treated with the percutaneous system 10 and/or the implanted system 11 by applying electrical stimulation using an IM lead directly to the effected area, e.g., motor point(s) within the muscle(s). The systems and methods may work by interfering with or blocking pain signals from reaching the brain.

An exemplary embodiment involves the treatment of post-stroke shoulder pain. The treatment of post-stroke shoulder pain with the percutaneous system 10 and/or the implanted system 11 may only provide temporary pain relief (as compared to permanent pain relief) once the therapy is completed. This is based on data summarized in a post-hoc analysis of the percutaneous electrical stimulation pilot study data (Chae, et al., 2007), which revealed that the most significant predictor of permanent pain relief was time since stroke onset. For patients treated less than 18 months after a stroke, pain was reduced significantly during electrical stimulation therapy and was maintained after the therapy was completed. However, for patients treated later than 18 months after a stroke, pain was reduced during electrical stimulation therapy but returned after the therapy was completed. Based on these data, a two product solution to treat post-stroke shoulder pain may be benefitial. The percutaneous system 10 may provide a temporary treatment for all patients. If the pain returns, patients could either choose to receive the temporary therapy again or receive a permanent therapy such as a fully implantable electrical stimulation system, which would be available for permanent treatment of post-stroke shoulder pain.

If the temporary therapy significantly reduces the shoulder pain, and the pain reduction is maintained after the therapy is discontinued, then the treatment is concluded. If the shoulder pain re-appears, either the percutaneous system 10 may be used again for temporary therapy or the chronic therapy system 11 can be implanted.

In the post-stroke shoulder pain example, the percutaneous system 10 stimulates the motor points of the middle and posterior deltoid muscles for the therapeutic treatment of shoulder pain by sending mild electrical pulses through one or more IM leads 12 placed near the motor points of these muscles (see FIGS. 2 and 3A). The mild electrical pulses from the percutaneous system 10 may also stimulate the axillary nerve, which innervates these muscles, thereby achieving the same therapeutic treatment of shoulder pain.

As previously described, percutaneous, intramuscular, electrical stimulation is less painful and better tolerated then surface electrical stimulation [Yu, et al., 2001b]. It is critical to the success of the therapy and overall patient compliance to be able to deliver the stimulation therapy in a comfortable and tolerable way.

Percutaneous, intramuscular electrical stimulation can be delivered at a lower stimulation frequency, which is associated with reduced muscle fatigue. Higher stimulation frequencies are used with surface electrical stimulation systems to minimize stimulation-induced pain. It is important to minimize the potential for muscle fatigue in post-stroke patients, so that they can still participate in the rehabilitation therapies for motor recovery.

The percutaneous system 10 may be intended to be used as a temporary stimulation therapy for post-stroke shoulder pain. One or more intramuscular leads 12 having electrodes 14 may be placed percutaneously in the shoulder via an insulated introducer needle 30. In one embodiment, one lead 12 may be placed near a middle position between the motor point of the Middle Deltoid, and the motor point of the Posterior Deltoid. In another embodiment, one lead 12 may be placed near the motor point of the Middle Deltoid, and another lead 12 may be placed near the motor point of the Posterior Deltoid. The percutaneous insertion site for one or both leads may be slightly inferior of the glenohumeral joint. One or both leads may be connected to the percutaneous system 10 which may be carried or placed (e.g., with adhesive or a strap) on the anterior portion of the upper arm.

This position of the percutaneous system 10 allows users and caregivers to operate the buttons 38 and see the display 40 during use. A surface electrode 24, or other known electrode types, may be connected to the stimulator and serve as the return electrode (anode). This surface electrode 24 may be placed adjacent to the stimulator. Its position is not critical to the therapy and it can be moved throughout the therapy to reduce the risk of skin irritation. The case of the implantable pulse generator 28 may serve as the return electrode in the fully implanted system 11.

III. Placing the IM Lead

Representative IM lead insertion techniques will now be described to place one or more IM lead(s) 12 in a desired location in muscle near the target motor point(s). It is this lead placement that makes possible the stimulation of the motor point(s) with one or more lead(s) 12 to provide pain relief.

Instructions for use 58 can direct use of systems and methods for the placement of an IM lead 12 in muscle near the motor point for improved recruitment of target nerves, e.g., with the placement of one or more leads 12. The instructions for use may include instructions for placing a lead 12 for the therapeutic electrical stimulation of the motor point in a system for the relief of pain, for example.

The instructions for use may also include instructions for recording stimulus parameters, including intensity associated with a first sensation of stimulation, a first noticeable muscle contraction, and a maximum tolerable contraction at one or more locations, which can be used to aid in determining desired stimulation parameters for optimal stimulation, for example, as will be described below.

To determine the optimal placement for the IM lead 12, test stimulation may be delivered through needle electrodes and muscle responses may be observed. The motor point(s) of the target muscle(s) may be located first in order to confirm that the muscles are innervated. Needle electrodes may be used because they can be easily repositioned until the optimal location to deliver stimulation is determined.

At least one lead(s) is desirably placed in muscle tissue near the muscle's motor point. Electrical stimulation is then applied to the motor point to determine if the peripheral nerve stimulation can block the sensation of pain in the area(s) of pain and/or reduce pain. The pain may be perceived to be contained within a specific part(s) of the body, e.g., the muscle in which the lead is placed.

Electrical stimulation may be applied to any motor point throughout the body, such as target motor points in muscles including, but not limited to deltoid (e.g., posterior, anterior, and/or middle) muscle, trapezius muscle, erector spinae, gastrocnemius, occipitailis, gluteus maximus, gluteus medius, iliotibial band, biceps femoris, adductor magnus, semitendinosus, gracilis, semimembranosus, sartorius, pectineus, adductor longus, vastus medialis, vastus lateralis, and rectus femoris.

Electrical stimulation may be delivered through a percutaneous and/or a fully implantable system(s). To determine if a person may benefit from stimulation, a person may be tested in the clinical setting (e.g. an office of a clinician, a laboratory, a procedure room, an operating room, etc.) and/or sent home and/or tested outside the clinical environment with external stimulator(s) connected to temporary percutaneous and/or surface electrodes. The trial period may range from minutes to hours to days to weeks to months, and in one embodiment the trial period may be between 3 and 21 days. Alternatively, it may be desirable to use a percutaneous system(s) as a therapy without proceeding to a fully implantable system. The duration of therapy for a percutaneous system may range from minutes to days to weeks to months to multiple years, and one embodiment includes a duration ranging from 1 to 12 weeks.

Regulated current is the preferred type of electrical stimulation, but other type(s) of stimulation (e.g. non-regulated current such as voltage-regulated) may also be used. Multiple types of intramuscular leads/electrodes may be used, including percutaneous and/or implantable. Surface electrodes may be a standard shape or they may be tailored if needed to fit the contour of the skin.

In a preferred embodiment of a percutaneous system, the surface-electrode(s) may serve as the anode(s) (or return electrode(s)), but the surface electrode(s) may be used as the cathode(s) (active electrode(s)) if necessary. When serving as a return electrode, the location of the electrode is not critical and may be positioned anywhere in the general vicinity, provided that the current path does not cross the heart. If a surface electrode serves as an active electrode, it (they) may be positioned near the target stimulation area(s), e.g., on the skin surface over the target motor point.

The IM lead may be placed near, but away from, the motor point(s) of the target muscle(s) and may be inserted via an introducer 30, which may be similar in size and shape to a hypodermic needle. The introducer may be any size. In one embodiment, the introducer may range in size from 17 g to 26 g.

Prior to inserting the introducer 30, the insertion site may be cleaned with a disinfectant (e.g., Betadine, 2% Chlorhexidine/80% alcohol, 10% povidone-iodine, or similar agent). A local anesthetic(s) may be administered topically and/or subcutaneously to the area in which the lead and/or introducer(s) will be inserted.

The motor point(s) may be electrically stimulated during and after placement of the lead. The lead may be placed via multiple types of approaches. In one embodiment, the approach(es) may be similar to a needle placement for electromyography (EMG).

Though peripheral nerve stimulation may have a success rate of over 80% and can almost completely eliminate pain in a majority of patients, the traditional method of surgically placing the lead(s) is time consuming and complex, which greatly limits its use outside of academic institutions (Long 1973; Nashold and Goldner 1975; Picaza et al. 1975; Nashold et al. 1982; Gybels and Van Calenbergh 1990). Thus, a major limitation of peripheral nerve stimulation is the lack of appropriate electrode lead(s) and a method(s) to place the electrode lead(s) near but away from peripheral target nerve(s) quickly and easily and such that the electrode(s) do not migrate (North 2003).

Methods for placing needle(s) for EMG may be adapted so that they can be used to place an IM lead near a motor point, with the lead inserted into muscle tissue such that the lead is in electrical proximity to but not touching the motor point. These improved methods will greatly simplify the lead placement procedure(s), making intramuscular motor point stimulation for the relief of pain feasible economically and clinically.

Previously, the clinicians (e.g. pain specialists and/or anesthesiologists) who typically see patients who may benefit from peripheral nerve stimulation had neither the time nor the training to perform the traditional time-consuming lead-placement procedure, e.g., an open surgery, previously required to place the lead(s) (e.g., cuff-type, spiral-type, and/or paddle-type leads) near the peripheral target nerves innervating the region(s) of pain. The systems and methods of the present invention adapt approaches for EMG so that they can be used to place an IM lead that is adapted to resist migration in muscle for the purpose stimulating a motor point for providing pain relief in the muscle region(s) where the lead is placed.

A. Instructions for Lead Placement

FIGS. 5 through 10 show representative embodiments of the steps that representative instructions for use 58 can incorporate or direct for the percutaneous placement of an IM lead 12 for the activation of a muscle A and muscle B (e.g., the middle and posterior deltoid muscles) in a system for the relief of pain, such as shoulder pain. The instructions may include a series of steps that can be followed to carry out portion or portions of the procedure. It is to be appreciated that these series of steps may be revised to place only one, or more than one IM lead(s) to activate one motor point in one muscle, or to activate two or more motor points in two or more muscles (see FIGS. 1A through 2).

In an exemplary embodiment, the steps may include, but are not limited to:

1) Clean and prepare the area above the muscle(s) in which the IM lead will be placed. For example, the lateral aspect of the affected shoulder may first be cleaned with Betadine, and a local subcutaneous anesthetic (e.g., 2% lidocaine) may be administered.

2) Locate the motor points of two adjacent muscles (A and B) and mark them, e.g., with an indelible marker. For example, the motor points of the middle and posterior heads of the deltoid muscle may be located using the standard locations for clinical electromyography (Lee and DeLisa, 2000).

3) Place a needle electrode (e.g., 24 G EMG needle electrode) at the identified motor point locations for muscle A and B. For example, needle electrode 20 is placed at motor point A and needle electrode 22 is placed at motor point B (see FIG. 6).

4) Place a surface stimulation return electrode 24 in proximity of the area where needle electrode 20 and 22 have been placed, which may also be in proximity of the area in which the percutaneous lead 12 will be placed. Test stimulation will be applied to each needle electrode 20 and 22 inserted in muscle A and muscle B respectively, with the surface electrode 24 providing a return path. The surface electrode 24 may be placed adjacent to the needle electrodes. Its position is not critical to the therapy and it can be moved throughout the therapy to reduce the risk of skin irritation.

Figure 7:
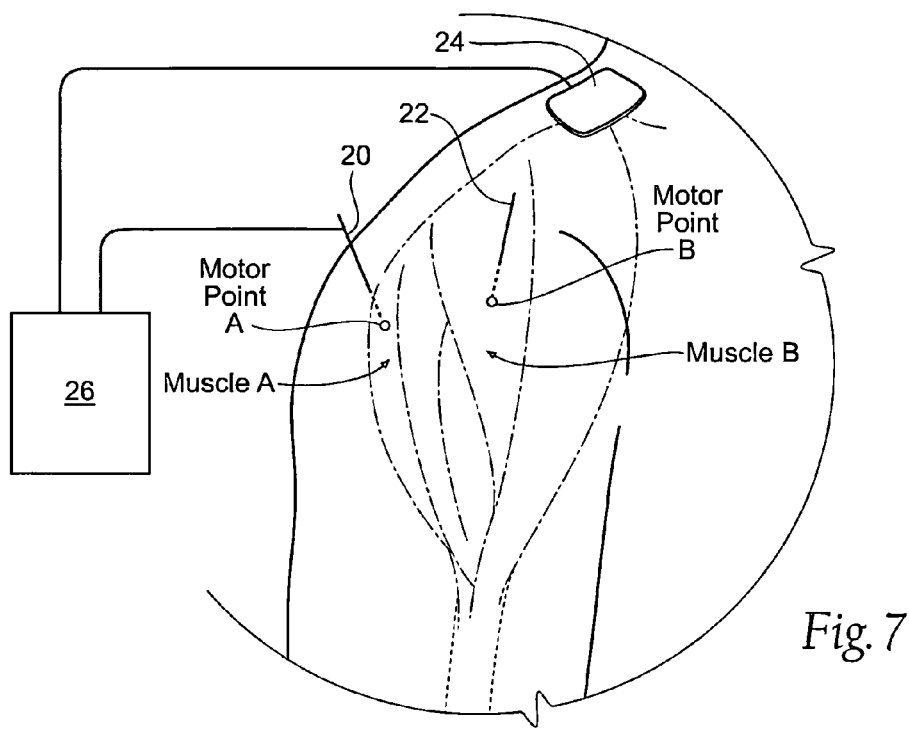
FIG. 7 is an anatomical view of the shoulder as shown in FIG. 6, showing a pulse generator coupled to one needle electrode and to the return electrode so that test stimulation may be delivered to stimulate the desired motor point.

5) Couple pulse generator 26 to one needle electrode and to the return electrode 24 (see FIG. 7). Set the desired stimulation parameters. Test stimulation may be delivered using a current-regulated pulse generator, for example.

6) Deliver stimulation to each needle electrode individually (i.e., one at a time) by slowly increasing the stimulation intensity. Stimulation intensity is defined here as the product of stimulation amplitude and stimulation pulse duration. Increasing the stimulation intensity can be achieved by keeping stimulation amplitude constant and increasing stimulation pulse duration, by keeping stimulation pulse duration constant and increasing stimulation amplitude, or by increasing both stimulation amplitude and stimulation pulse duration. For example, the stimulation intensity may initially be set at a very small, sub-sensation and sub-motor threshold level. Then, the stimulation intensity may be increased in small increments (e.g. 10 μs) to determine thresholds, for each motor point, at which the first sensation of stimulation occurs ($T_{SEN}$, stimulation evokes the first visible muscle contraction (motor threshold, $T_{MUS}$) and stimulation evokes the maximum tolerable muscle contraction ($T_{MAX}$).

7) Each needle location may need to be adjusted to a location that provides the strongest muscle contraction at the lowest stimulation intensity for each muscle. If the thresholds measured are determined to be high, it may be an indicator that the electrode is placed too far away from the motor point. Placing the electrode closer to the motor point, but not touching the motor point, may reduce one or more thresholds, and the motor point may be found when the threshold measurements are at a desired minimum. For example, if $T_{MUS}$ is close to $T_{MAX}$, the needle electrode may be repositioned to lower the threshold such that $T_{MUS} \ll T_{MAX}$, thus allowing for a strong contraction below the maximum tolerable stimulus intensity.

8) Record the stimulation intensity at which the first sensation, first noticeable muscle contraction, and maximum tolerable muscle contraction occurs for both muscle A and muscle B.

Figure 8:
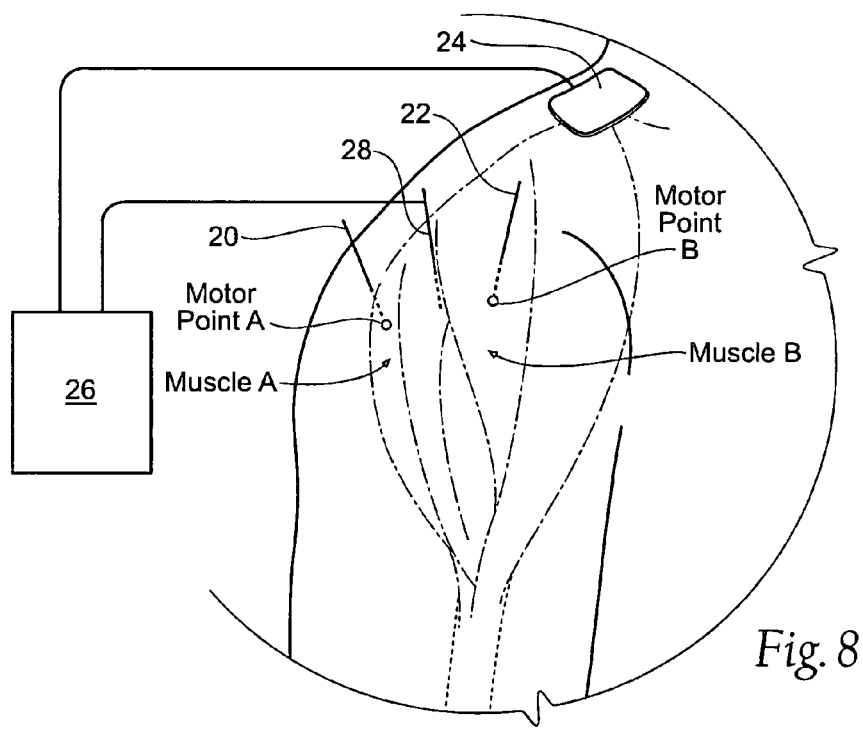
FIG. 8 is an anatomical view of the shoulder as shown in FIG. 6, showing the location at which both muscle A and muscle B can be activated simultaneously using one electrode, by placing a needle electrode at the approximate midpoint between the prior identified locations of needle electrodes for muscle A and muscle B respectively.
Figure 9:
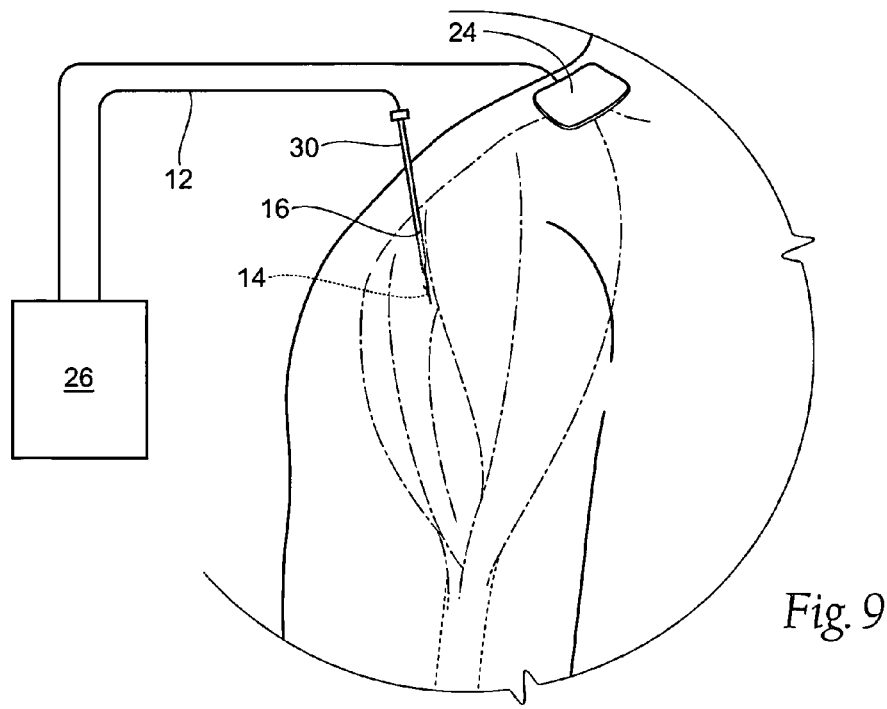
FIG. 9 is an anatomical view of the shoulder as shown in FIG. 6, showing the intramuscular lead 12 and electrode 14 placed percutaneously in the shoulder via an introducer needle.
Figure 10:
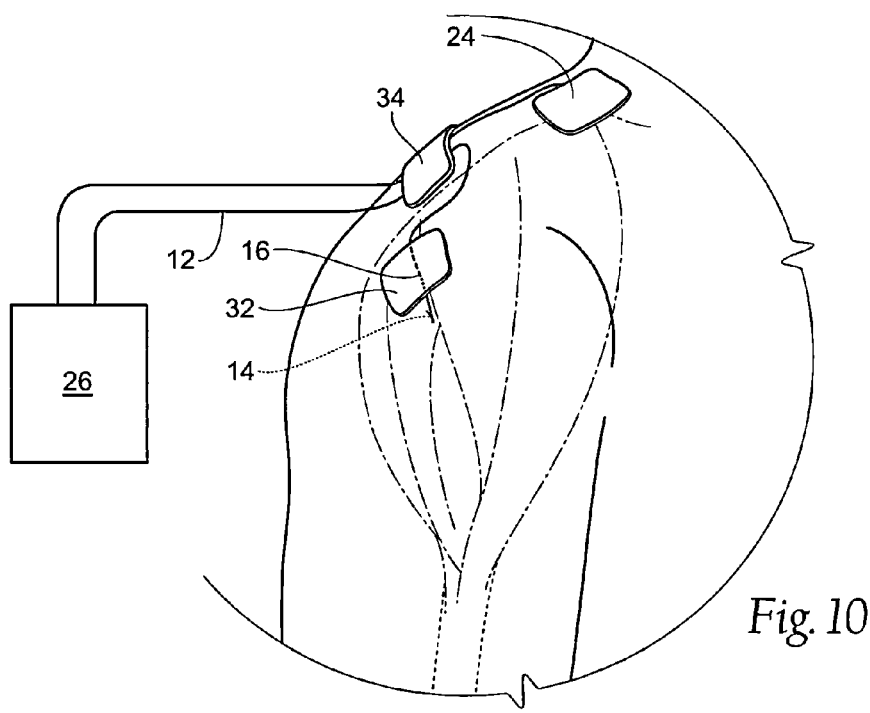
FIG. 10 is an anatomical view of the shoulder as shown in FIG. 6, showing the percutaneous exit site and lead 12 covered with a bandage 32, and an additional bandage 34 is shown to secure the external portion of the lead 12 (or an extension cable used to couple the lead 12 to the external pulse generator) to the skin.

9) Determine the location at which both muscle A and muscle B can be activated simultaneously using one electrode, by placing a needle electrode 28 at the approximate midpoint between the above identified locations of needle electrodes 20, 22 for the motor points of muscle A and muscle B respectively (see FIG. 8).

10) Deliver stimulation to the needle electrode 28 in an attempt to activate both muscle A and muscle B with the one electrode. For example, deliver stimulation, increasing stimulation intensity until both the middle and posterior deltoids muscles (i.e., muscle A and muscle B) are activated and are producing strong, visible, and palpable muscle contraction at a tolerable stimulus intensity.

11) If unable to achieve strong contraction of both muscles A and B at a tolerable stimulus intensity, remove the electrode 28 and place it a predetermined distance (e.g., approximately 0.5 cm) closer to the muscle that shows weaker contraction.

12) Repeat stimulation delivery and placement location correction until both muscle A and muscle B contract at the desired level at a tolerable stimulus intensity.

13) Mark this location with an indelible marker.

14) Record at which stimulation intensity first sensation, first noticeable muscle contraction, and maximum tolerable muscle contraction occurs.

At this point in the process, three parameters, $T_{sen}$, $T_{mus}$, and $T_{max}$ have been measured for the three locations, i.e., motor point of muscle A, motor point of muscle B, and the optimal location between motor point of muscle A and B to activate both muscles. It is expected that the three parameters may be higher for the location in the middle due to its larger relative distance to the motor points at location A and B compared to both individual locations A and B.

For the described one lead approach, the parameters at location A and B may be used for guiding the exploration of finding the ideal location between A and B and the expected parameter range for the middle location. The parameters at the middle location are then used to program the parameters for the one lead placed in the middle depending on the desired application. An application might require sub-sensation stimulation, an application might require sub-motor (but supra-sensation) stimulation, an application might require supra-motor threshold stimulation, and yet another application might require stimulation at the maximum tolerable level. For example, the pain relief application described may require stimulation at $T_{max}$ in the middle location to activate the posterior and middle deltoid fully at the maximum tolerable stimulation intensity.

15) Remove all three needle electrodes 20, 22, and 28.

16) Identify the anticipated pathway of the percutaneous lead 12. The entry point of the lead may be a predetermined distance (e.g., approximately 2 to 3 cm) above the site identified as the location for the placement between the muscles A and B, such that the lead enters tangentially, for example. This placement may aid in lead stability.

17) Administer a local anesthetic (e.g., 2% lidocaine) at the skin surface and along the anticipated pathway of the lead 12.

18) Insert the percutaneous lead 12 and electrode 14. For example, the lead may be placed percutaneously in the muscle-via an insulated 20 G introducer needle 30 (see FIG. 9).

19) Once the electrode 14 of the lead 12 has reached the marked location (i.e., at or near the final position of needle electrode 28), couple pulse generator 26 to the lead 12 and to the return electrode 24, and deliver stimulation to the lead 12 to verify proper placement. Both muscle A and muscle B desirably contract. Desirably, a strong, visible, and palpable contraction is evoked at a stimulus intensity that is tolerable for the participant.

Although not required, the position of the IM lead may be checked by imaging techniques, such as ultrasound or X-rays (fluoroscopy). Following placement of the lead(s), the portion of the leads which exit the skin may be secured to the skin using covering bandages and/or adhesives.

20) The stimulation intensity associated with first sensation of stimulation (i.e., $T_{SEN}$), first noticeable muscle contraction (i.e., $T_{MUS}$), and maximum tolerable contraction (i.e., $T_{MAX}$), may again be recorded.

21) Turn off stimulation and secure the lead to the skin.

22) Cover the percutaneous exit site 16 and lead 12 with a bandage 32. A bandage 34 may also be used to secure the external portion of the lead 12 (or an extension cable used to couple the lead 12 to the external pulse generator) to the skin (see FIG. 10). It is anticipated that the length of time to identify the optimal placement and place the IM lead to be less than one hour.

It is possible that stimulation intensity may need to be adjusted, i.e., increased or decreased slightly during the treatment period due to causes such as habituation or the subject becoming accustomed to sensation, but the need for increased or decreased intensity is unlikely and usually only occurs after several days to weeks to months as the tissue encapsulates and the subject accommodates to stimulation (Nashold 1975; Krainick and Thoden 1981; Goldman et al. 2008). It is to be appreciated that the need for increased intensity could happen at any time, even years out, which would likely be due to either lead migration or habituation, but may also be due reasons ranging from nerve damage to plasticity/reorganization in the central nervous system.

If stimulation is successful, i.e., if the screening test and/or home-trial are successful, the patient's percutaneous system 10 may be converted into a fully implanted system 11 by replacing the external pulse generator 26 with an implantable pulse generator 28 that is implanted in a convenient area (e.g., in a subcutaneous pocket over the hip or in the subclavicular area).

In one embodiment, the IM lead 12 used in the screening test and/or home-trial may be totally removed and discarded, and a new completely implantable lead may be tunneled subcutaneously and coupled to the implantable pulse generator. In an alternative embodiment, a two part lead may be incorporated in the screening test and/or home-trial where the implantable part is completely under the skin and connected to a percutaneous connector (i.e., extension) that can be discarded after removal. The implantable part may then be tunneled and coupled to the implantable pulse generator, or a new sterile extension may be used to couple the lead to the implantable pulse generator, for example.

IV. Lead and Electrode Configurations

It is to be appreciated that the configuration of one or more leads 12 and electrodes 14, and the manner in which they are implanted can vary. Representative embodiment(s) will be described, with reference to FIGS. 11A through 12B.

Stimulation may be applied through an IM lead 12, such as a fine wire intramuscular lead and electrode, inserted via a needle introducer or surgically implanted in proximity of the target site. Once proper placement is confirmed, the needle may be withdrawn, leaving the lead in place, i.e., in muscle in proximity to the motor point. Stimulation may also be applied through a penetrating electrode, such as an electrode array comprised of any number (i.e., one or more) of needle-like electrodes that are inserted into the target site. Non-limiting examples of such micro electrode arrays include Michigan or Utah arrays. In both cases, the lead may placed using a needle-like introducer 30, allowing the lead/electrode placement to be minimally invasive.

In one embodiment, the lead 12 may comprise a thin, flexible component made of a metal and/or polymer material. By "thin," it is contemplated that the lead may not be greater than about 0.75 mm (0.030 inch) in diameter, although it is to be appreciated that the lead may have a larger or smaller diameter.

The lead 12 can comprise, e.g., one or more coiled metal wires within an open or flexible elastomer core. The wire can be insulated, e.g., with a biocompatible polymer film, such as polyfluorocarbon, polyimide, or parylene. The lead is desirably coated with a textured, bacteriostatic material, which helps to stabilize the lead in a way that still permits easy removal at a later date and increases tolerance.

The lead 12 may be electrically insulated everywhere except at one (monopolar) (see FIG. 11A), or two (bipolar), or four (quadpolar) (see FIG. 11B), or more, for example, electrodes 14, i.e., conduction locations, near the lead's distal tip. Each of the electrode(s) may be connected to one or more conductors that run the length of the lead 12, proving electrical continuity from the electrode through the lead 12 to the stimulator 26 or 28.

The electrode(s) may comprise a de-insulated area of an otherwise insulated conductor that runs the length of an entirely insulated electrode. The de-insulated conduction region of the conductor can be formed differently, e.g., it can be wound with a different pitch, or wound with a larger or smaller diameter, or molded to a different dimension. The electrode may comprise a separate material (e.g., metal or a conductive polymer) exposed to the body tissue to which the conductor of the wire is bonded.

The IM lead 12 is desirably provided in a sterile package, and may be pre-loaded in the introducer needle 30. The lead 12 desirably possess mechanical properties in terms of flexibility and fatigue life that provide an operating life free of mechanical and/or electrical failure, taking into account the dynamics of the surrounding muscle tissue (i.e., stretching, bending, pushing, pulling, crushing, etc.). The material of the electrode may discourage the in-growth of connective tissue along its length, so as not to inhibit its withdrawal at the end of its use. However, it may be desirable to encourage the in-growth of connective tissue at the distal tip of the electrode, to enhance its anchoring in tissue.

Figure 11A:
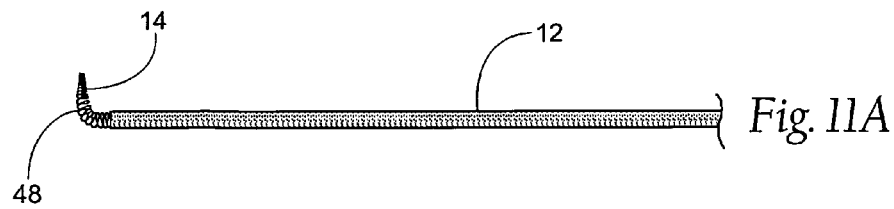
FIGS. 11A and 11B are plan views of a possible intramuscular lead having one electrode or more than one electrode for use with the systems and methods of the present invention, the lead including one or more anchoring members.
Figure 11B:
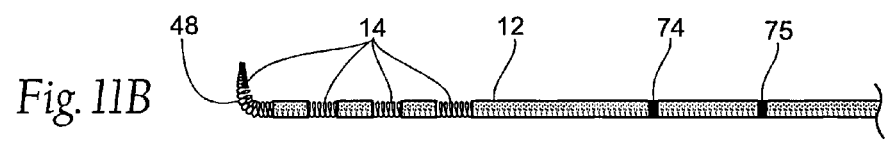

One embodiment of the lead 12 shown in FIGS. 11A and 11B may comprise a minimally invasive coiled fine wire lead 12 and electrode 14. The electrode 14 may also include, at its distal tip, an anchoring element 48. In the illustrated embodiment, the electrode 14 is the anchoring element 48, which takes the form of a simple barb or bend. The electrode may be bent to serve the dual purpose of the anchoring barb and the stimulating electrode. The anchoring element 48 may be sized and configured so that, when in contact with tissue, it takes purchase in tissue, to resist dislodgement or migration of the electrode out of the correct location in the surrounding tissue. Desirably, the anchoring element 48 is prevented from fully engaging body tissue until after the electrode 14 has been deployed. The electrode may not be deployed until after it has been correctly located during the implantation (lead placement) process, as previously described.

Figure 12A:
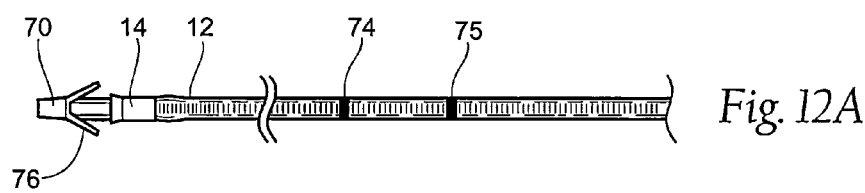
FIGS. 12A and 12B are plan views of another possible intramuscular lead having one electrode or more than one electrode for use with the systems and methods of the present invention, the lead including one or more anchoring members.
Figure 12B:
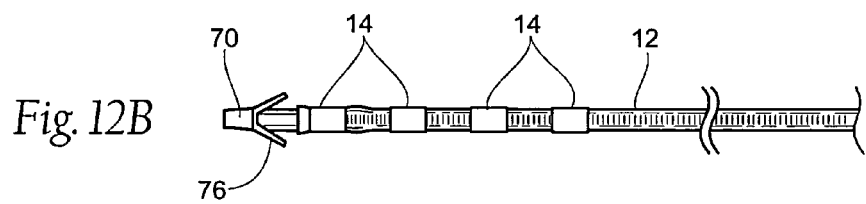

Alternative embodiments of an IM lead 12 shown in FIGS. 12A and 12B may also include at or near its distal tip or region, one or more anchoring element(s) 70. In the illustrated embodiment, the anchoring element 70 takes the form of an array of shovel-like paddles or scallops or tabs 76 distal to the distal-most electrode 14, although a tab 76 or tabs could also be proximal to the distal and/or proximal most electrode 14. The tabs 76 as shown are sized and configured so they will not cut or score the surrounding tissue. The anchoring element 70 is sized and configured so that, when in contact with the muscle tissue, it takes purchase in the muscle, to resist dislodgement or migration of the electrode out of the correct location in the surrounding muscle. In one embodiment, the anchoring element 70 may be prevented from fully engaging body tissue until after the electrode 14 has been deployed. The electrode may not be deployed until after it has been correctly located during the implantation (lead placement) process, as previously described. In addition, the lead 12 may include one or more ink markings 74, 75 to aid the physician in a predetermined placement.

FIGS. 12A and 12B show the lead 12 may be electrically insulated everywhere except at one (monopolar) (See FIG. 12A), or two (bipolar), or four (quadpolar) (see FIG. 12B), or more, for example, electrodes 14, i.e., conduction locations, near the lead's distal tip. Each of the electrode(s) may be connected to one or more conductors that run the length of the lead 12, proving electrical continuity from the electrode through the lead 12 to the stimulator 26 or 28.

Alternatively, or in combination, stimulation may be applied through any type of nerve cuff (spiral, helical, cylindrical, book, flat interface nerve electrode (FINE), slowly closing FINE, etc.), paddle (or paddle-style) electrode lead, cylindrical electrode lead, and/or other lead that is surgically or percutaneously placed within muscle at the target site.

In all cases, the lead may exit through the skin and connect with one or more external stimulators 26, or the lead(s) may be routed subcutaneously to one or more implanted pulse generators 28, or they may be connected as needed to internal and external coils for RF (Radio Frequency) wireless telemetry communications or an inductively coupled telemetry to control the implanted pulse generator. The implanted pulse generator 28 may be located some distance (remote) from the electrode 14, or an implanted pulse generator may be integrated with an electrode(s), eliminating the need to route the lead subcutaneously to the implanted pulse generator.

In one embodiment, the lead 12 can include a metal stylet within its core. Movement of the stylet with respect to the body of the lead 12 and/or an associated introducer 30 (if used) may be used to deploy the lead 12 by exposing the anchoring element 48, 70 to body tissue. In this arrangement, the stylet is removed once the lead 12 is located in the desired region.

Figure 13:
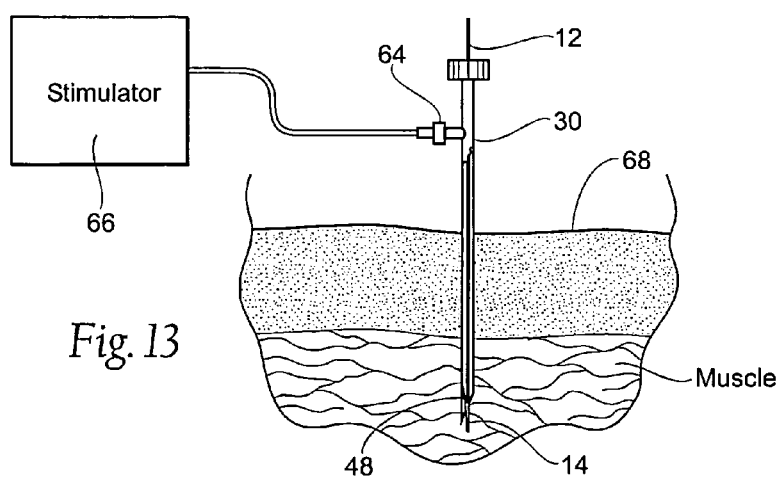
FIGS. 13 to 15 show the use of a lead introducer to percutaneously implant an intramuscular lead in a targeted muscle region and for connection to a lead extension.
Figure 14:
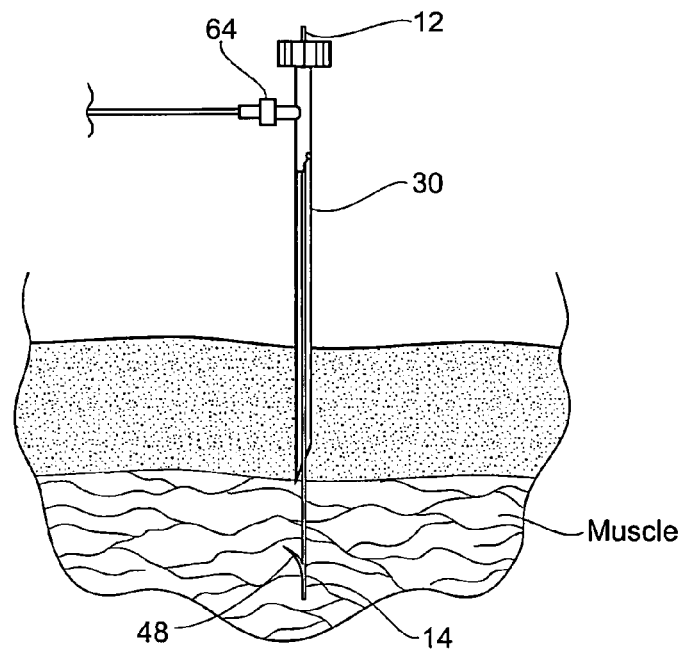
Figure 15:
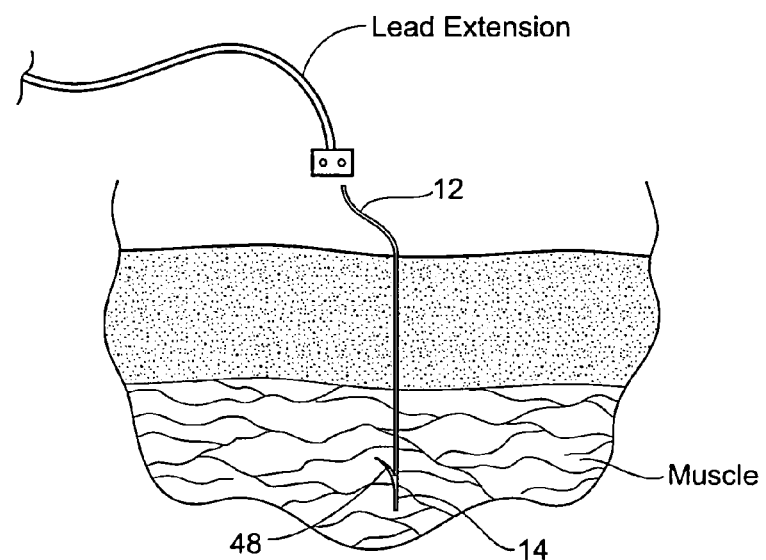

In another embodiment (see FIGS. 13 through 15), the lead 12 may be percutaneously implanted housed within introducer 30 (i.e., a hypodermic needle). The introducer 30 comprises a shaft having sharpened needle-like distal tip, which penetrates skin and tissue leading to the targeted muscle region. The lead 12 is loaded (it may be preloaded and provided in a kit) within a lumen in the introducer 30, with the anchoring element 48, 70 shielded from full tissue contact within the shaft of the introducer 30 (see FIG. 13). In this way, the introducer can be freely manipulated in tissue in search of a desired final implantation site (see FIG. 14) before deploying the lead 12 and withdrawing the introducer 30 (see FIG. 15).

The introducer 30 may be insulated along the length of the shaft, except for those areas that correspond with the exposed conduction surfaces of the electrode 14 housed inside the introducer 30. These surfaces on the outside of the introducer 30 are electrically isolated from each other and from the shaft of the introducer 30. These surfaces may be electrically connected to a connector 64 at the end of the introducer body (see FIGS. 13 and 14). This allows connection to a stimulating circuit 66 (see FIG. 13) during the implantation process. The stimulating circuit 66 may comprise a stand alone stimulator, or the external pulse generator 26 may be the stimulating circuit. Applying stimulating current through the outside surfaces of the introducer 30 provides a close approximation to the response that the electrode 14 will provide when it is deployed at the current location of the introducer 30.

The introducer 30 may be sized and configured to be bent by hand prior to its insertion through the skin. This will allow the physician to place lead 12 in a location that is not in an unobstructed straight line with the insertion site. The construction and materials of the introducer 30 allow bending without interfering with the deployment of the lead 12 and withdrawal of the introducer 30, leaving the lead 12 in the tissue.

V. Stimulation Parameters

Control of the stimulator and stimulation parameters may be provided by one or more external controllers. In the case of an external stimulator, the controller may be integrated with the external stimulator. The implanted pulse generator external controller (i.e., clinical programmer) may be a remote unit that uses RF (Radio Frequency) wireless telemetry communications (or an inductively coupled telemetry) to control the implanted pulse generator. The external or implantable pulse generator may use passive charge recovery to generate the stimulation waveform, regulated voltage (e.g., 10 mV to 20 V, or more or less), and/or regulated current (e.g., about 10 µA to about 50 mA, or more or less). Passive charge recovery is one method of generating a biphasic, charge-balanced pulse as desired for tissue stimulation without severe side effects due to a DC component of the current.

Figure 16:
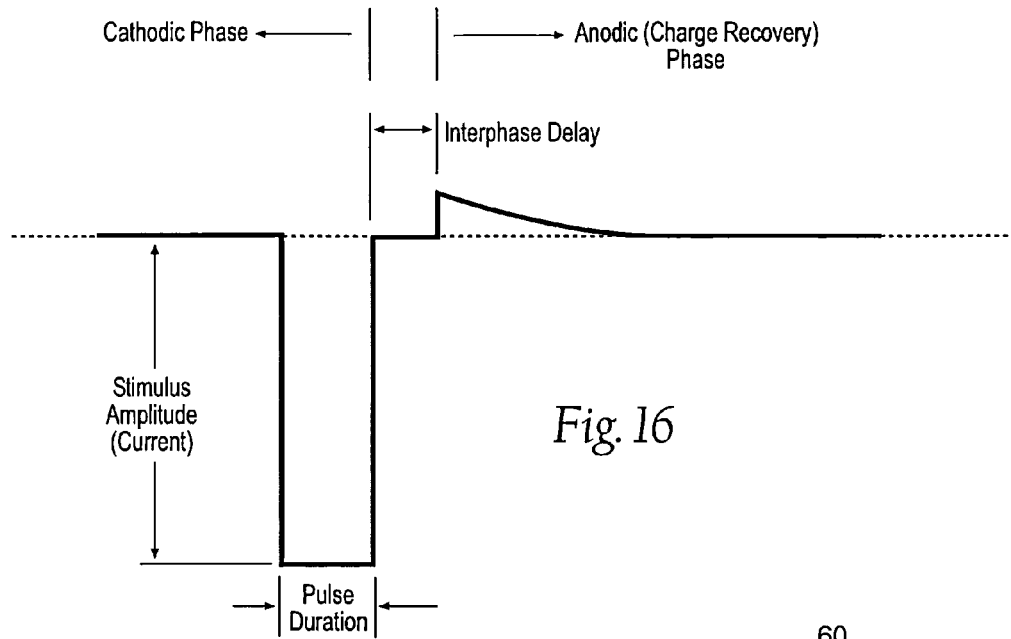
FIG. 16 is a graphical view of a possible biphasic stimulus pulse output of the external and/or implantable pulse generators for use with the system shown in FIGS. 3A through 4B.

A desired stimulation pulse may by cathodic stimulation, although anodic will work, biphasic although monophasic and/or multi-phasic will work, and asymmetrical, although symmetrical will work. Its shape may be rectangular or exponential or a combination of rectangular and exponential waveforms. The pulse width of each phase may range between e.g., about 0.1 µsec. to about 1.0 sec., or more or less, as non-limiting examples. See FIG. 16 for a representative stimulation pulse.

Pulses may be applied in continuous or intermittent trains (i.e., the stimulus frequency changes as a function of time). In the case of intermittent pulses, the on/off duty cycle of pulses may be symmetrical or asymmetrical, and the duty cycle may be regular and repeatable from one intermittent burst to the next or the duty cycle of each set of bursts may vary in a random (or pseudo random) fashion. Varying the stimulus frequency and/or duty cycle may assist in warding off habituation because of the stimulus modulation.

The stimulating frequency may range from, e.g., about 1 Hz to about 300 Hz, or about 1 Hz to about 150 Hz, or about 1 Hz to about 50 Hz, or about 12 Hz to about 16 Hz, or more or less, and the frequency of stimulation may be constant or varying. In the case of applying stimulation with varying frequencies, the frequencies may vary in a consistent and repeatable pattern or in a random (or pseudo random) fashion or a combination of repeatable and random patterns.

The stimulator intensity may range from, e.g., about 1.0 mA to about 2 mA, or about 0.1 mA to about 40 mA, or about 0.01 mA to about 200 mA, or more or less, and about 100 µsec to about 300 µsec, or about 40 µsec to about 1000 µsec, or about 1 µsec to about 10,000 µsec, or more or less, sufficient to activate the target motor point at some distance X1 mm away from the motor point. If the stimulus intensity is too great, it may generate muscle twitch(es) or contraction(s) sufficient to disrupt correct placement of the lead. If stimulus intensity is too low, the lead may be advanced too close to the motor point and possibly beyond the optimal position, possibly leading incorrect guidance, nerve damage, mechanically evoked sensation (e.g., pain and/or paresthesia) and/or muscle contraction (i.e., when the lead touches the nerve), inability to activate the target nerve fiber(s) without activating non-target nerve fiber(s), improper placement, and/or improper anchoring of the lead, e.g., the lead may be too close to the nerve and no longer able to anchor appropriately in the muscle tissue.

The stimulator may be set to a frequency range from, e.g., about 0.5 Hz to about 12 Hz, or about 0.1 Hz to about 20 Hz, or about 0.05 Hz to about 40 Hz, or more or less, and is desirably low enough to evoke visible muscle twitches, i.e., non-fused muscle contraction, and/or muscle contraction(s) of the target muscle(s) innervated by the target nerve(s) but high enough that that the target motor point will be activated before the lead is advanced beyond the optimal position.

While stimulation is being applied, the lead (non-limiting examples of the lead could include a single or multi-contact electrode that is designed for temporary (percutaneous) or long-term (implant) use or a needle electrode (used for in-office testing only)) may be advanced, e.g., slowly advanced, towards the target motor point until the desired indicator response, e.g., muscle twitch, muscle contraction, and/or some combination, is obtained. The intensity may then be decreased, e.g., gradually decreased, as the lead is advanced closer to the target motor point until the desired indicator response(s) may be obtained at smaller intensity(ies) within the target range, e.g., about 0.1 mA to about 1.0 mA, or about 0.09 mA to about 39 mA, or about 0.009 mA to about 199 mA, or more or less, and about 100 µsec to about 300 µsec, or about 40 µsec to about 1000 µsec, or about 1 µsec to about 10,000 µsec, or more or less at some distance X2 mm, where X2<X1, and (as a non-limiting example) X1 may be multiple times larger than X2, such as X1≥2*X2, or X1≥5*X2, or X1≥20*X2, from the target nerve. As a non-limiting example, if the intensity is initially set to 1-1.5 mA (at a lead-to-nerve distance of X1), then it may be anticipated to get the same response at an intensity of 0.3-0.5 mA as the lead is advanced to a distance of X2 from the nerve. This assumes that the pulse width is left constant. It is to be appreciated that the amplitude (mA) may be left constant and decrease pulse width (us) as the lead is advanced, but regardless, the effect of decreasing stimulation intensity while advancing towards the nerve is the same.

If a specific response(s), including a desired response(s) and/or undesired response(s) can be obtained at a range of intensities that are too low, then the lead may be located in a non-optimal location (e.g., too close to the target motor point(s)). Non-limiting examples of ranges of intensities that may be considered too low include those that are a fraction, e.g., <⅔, or <⅕, or <1/10 of the intensities that obtained the desired response(s) at the distance X1.

The preferred stimulus intensities are a function of many variables, are meant to serve as non-limiting examples only, and may need to be scaled accordingly. As an example, if electrode shape, geometry, or surface area were to change, then the stimulus intensities may need to change appropriately. For example, if the intensities were calculated for a lead with an electrode surface area of approximately 20 mm$^2$, then they may need to be scaled down accordingly to be used with a lead with an electrode surface area of 0.2 mm$^2$ because a decrease in stimulating surface area may increase the current density, increasing the potential to activate excitable tissue (e.g., target and non-target nerve(s) and/or fiber(s)). Alternatively, if the intensities were calculated for a lead with an electrode surface area of approximately 0.2 mm$^2$, then the intensities may need to be scaled up accordingly to be used with a lead with an electrode surface area of 20 mm$^2$. Alternatively, stimulus intensities may need to be scaled to account for variations in electrode shape or geometry (between or among electrodes) to compensate for any resulting variations in current density. In a non-limiting example, the electrode contact surface area may be 0.1 mm$^2$ to about 20 mm$^2$, or 0.01 mm$^2$ to about 40 mm$^2$, or 0.0001 mm$^2$ to about 1000 mm$^2$. In a non-limiting example, the electrode contact configuration may include one or more of the following characteristics: cylindrical, conical, spherical, hemispherical, circular, triangular, trapezoidal, raised (or elevated), depressed (or recessed), flat, and/or borders and/or contours that are continuous, intermittent (or interrupted), and/or undulating.

Stimulus intensities may need to be scaled to account for biological factors, including but not limited to patient body size, weight, mass, habitus, age, and/or neurological condition(s). As a non-limiting example, patients that are older, have a higher body-mass index (BMI), and/or neuropathy, e.g., due to diabetes, may need to have stimulus intensities scaled higher (or lower) accordingly (Bigeleisen et al. 2009). Bigeleisen et al. indicated that a stimulation intensity of 0.2 mA and 100 μsec indicates intraneural lead placement, i.e., the lead/electrode is too close to the nerve because the lead is inside the nerve. The lead was a 22 gauge, 5 cm stimulating needle made by B. Braun, Bethlehem, Pa. From the above example, a calculation of the surface area of the stimulating electrode would provide representative data needed to scale stimulus intensities accordingly for larger or smaller contact areas.

As mentioned above, if the IM lead is too far away from the target motor point(s), then stimulation may be unable to evoke the desired response(s), e.g., muscle contraction(s), and/or pain relief, in the desired region(s) at the desired stimulus intensity(ies). If the lead is too close to the target motor point(s), then stimulation may be unable to evoke the same or similar desired response(s) in the desired region(s) at the desired stimulus intensity(ies) without evoking undesirable response(s), such as unwanted and/or painful muscle contraction(s), sensation(s), paresthesia(s), increase in pain, and/or generation of additional pain in related or unrelated area(s).

In some cases, it may be difficult to locate the optimal IM lead placement or distance from the target motor point(s) and/or it may be desirable to increase the range of stimulus intensities that evoke the desired response(s) without evoking the undesired response(s) so alternative stimulus waveforms and/or combinations of leads and/or electrode contacts may be used. A non-limiting example of alternative stimulus waveforms may include the use of a pre-pulse to increase the excitability of the target fiber(s) and/or decrease the excitability of the non-target fiber(s).

Those skilled in the art will recognize that, for simplicity and clarity, the full structure and operation of all systems and methods suitable for use with the present invention is not being depicted or described herein. Instead, only so much of an external and implantable pulse generator and supporting hardware as is unique to the present invention or necessary for an understanding of the present invention is depicted and described. The remainder of the construction and operation of the pulse generators described herein may conform to any of the various current implementations and practices known in the art.

VI. System Kits

Figure 17:
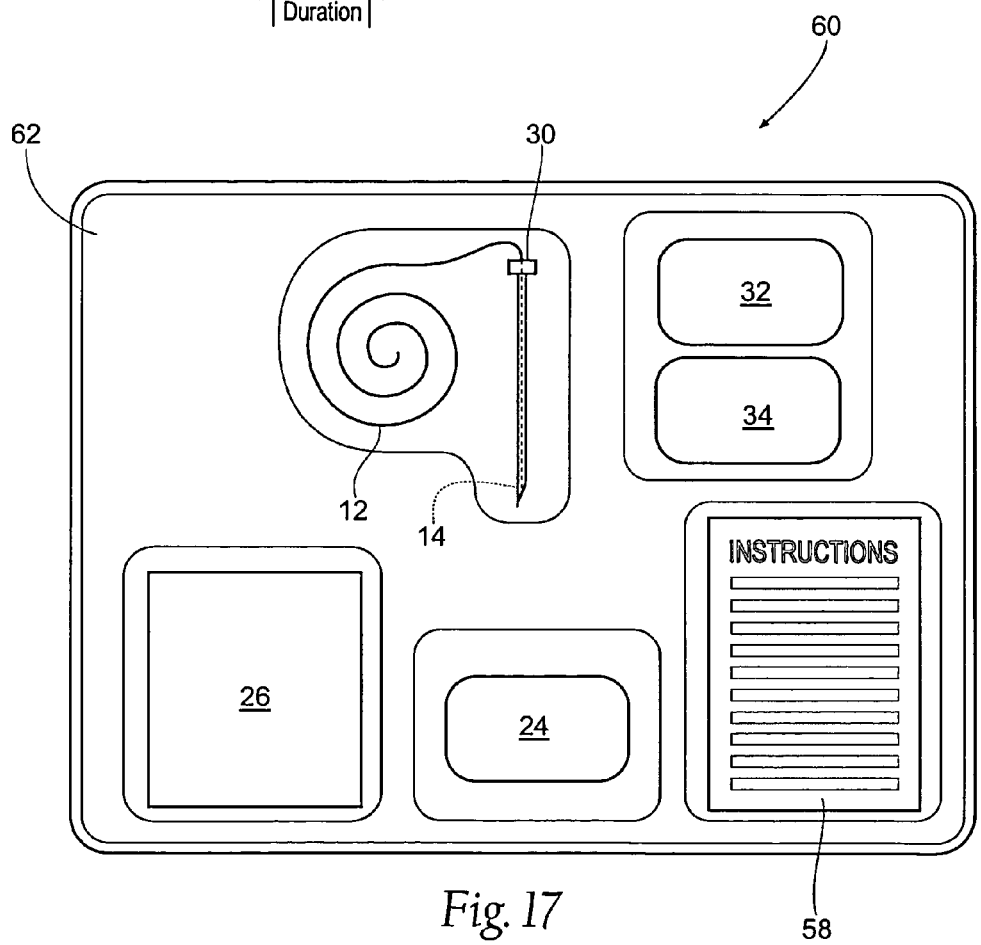
FIG. 17 is a plan view of a kit packaging the systems and methods components for use, along with instructions for use.
Figure 18:
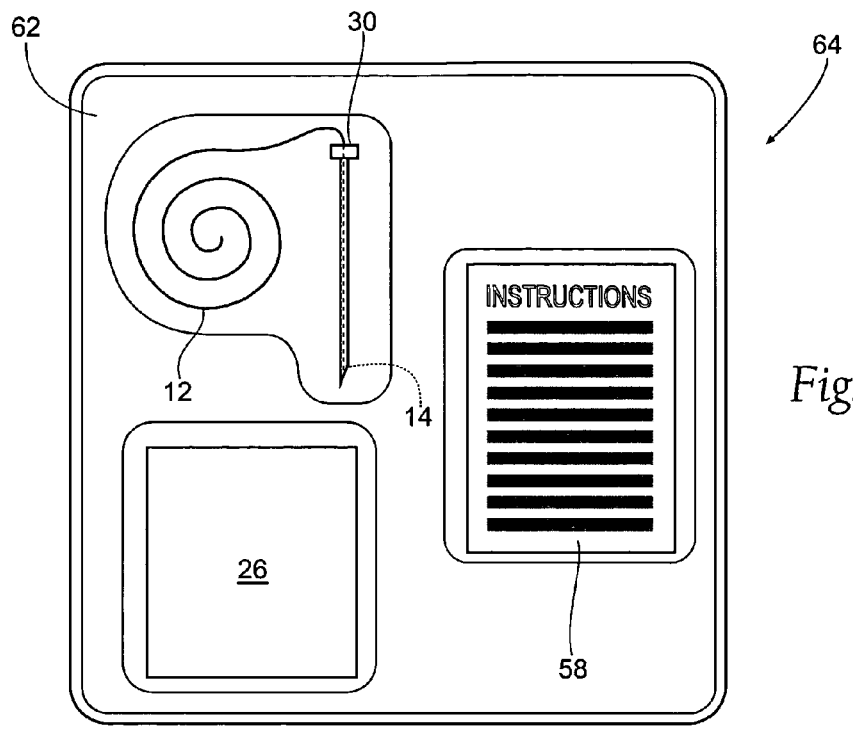
FIG. 18 is a plan view of another embodiment of a kit packaging the systems and methods components for use, along with instructions for use.
Figure 19:
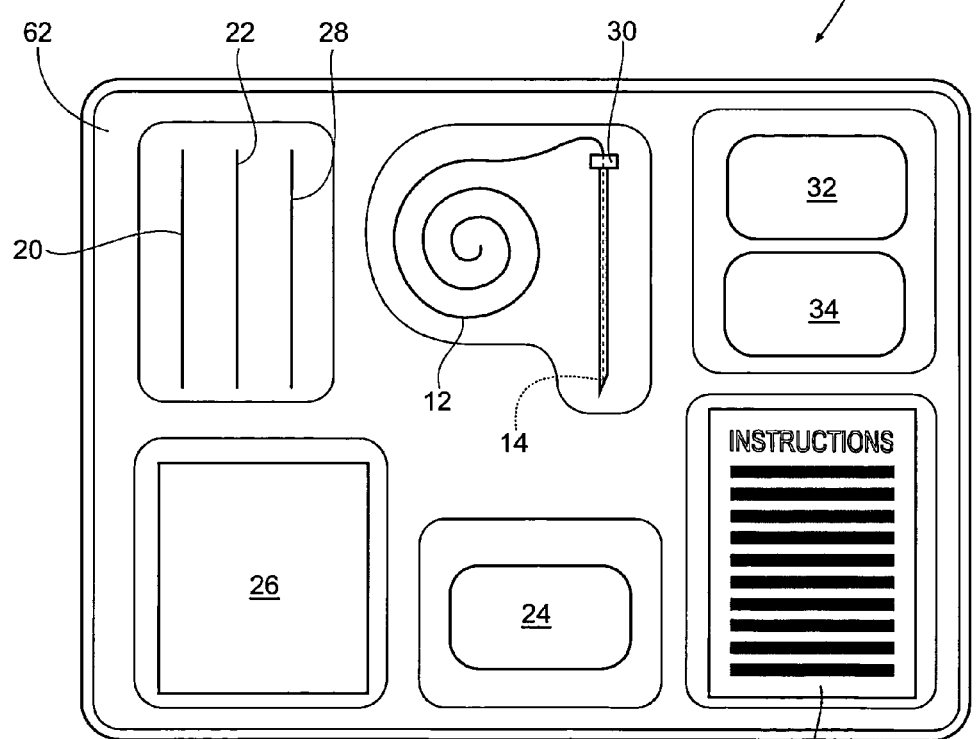
FIG. 19 is a plan view of another embodiment of a kit packaging the systems and methods components for use, along with instructions for use.

As FIGS. 17 and 18 show, the various devices and components just described can be consolidated for use in one or more functional kit(s) 60, 64, 68. The kits can take various forms and the arrangement and contents of the kits can vary. In the illustrated embodiments, each kit 60, 64, 68 comprise a sterile, wrapped assembly. Each kit 60, 64, 68 includes an interior tray 62 made, e.g., from die cut cardboard, plastic sheet, or thermo-formed plastic material, which hold the contents. Kits 60, 64, 68 also desirably includes instructions for use 58 for using the contents of the kit to carry out the procedures described above, including the systems and methods incorporating the percutaneous system 10 and/or the implanted system 11.

The instructions 58 can, of course vary. The instructions 58 may be physically present in the kits, but can also be supplied separately. The instructions 58 can be embodied in separate instruction manuals, or in video or audio tapes, CD's, and DVD's. The instructions 58 for use can also be available through an internet web page.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:
1. A method to alleviate pain, the method comprising:
identifying a tissue region where pain is perceived including skeletal muscle innervated by a peripheral nerve and including a motor point, wherein identifying the tissue region includes locating the motor point by percutaneously placing a locating lead and applying the therapeutic electrical stimulation to the locating lead and adjusting the position of the locating lead until a muscle twitch is observed in the skeletal muscle and the motor point is located without any verbal feedback from the patient;

placing at least one intramuscular lead having at least one electrode within the skeletal muscle in electrical proximity, the motor point, and applying therapeutic electrical stimulation to the at least one electrode according to predefined therapeutic electrical stimulation parameters to affect afferent and/or efferent nerve stimulation within the skeletal muscle and to provide the therapeutic electrical stimulation to the motor point to alleviate pain without any functional nerve stimulation involving the skeletal muscle.

2. A method according to claim 1:
wherein the steps to place the intramuscular lead percutaneously near the motor point and to evoke a muscle contraction are accomplished between about one minute and about thirty minutes.

3. A method according to claim 1, wherein the locating lead is one of the at least one intramuscular lead.

4. A method comprising:
placing a first lead in electrical proximity to a first motor point of a first muscle,
placing a second lead in electrical proximity to a second motor point of a second muscle,
placing a third lead in electrical proximity to a point generally in-between the first lead in electrical proximity to the first motor point of the first muscle and the second lead in electrical proximity to the second motor point of the second muscle, and
providing electrical stimulation to the third lead to activate the motor point of the first muscle and the motor point of the second muscle.

5. A method according to claim 4:
wherein the first muscle and the second muscle are activated simultaneously.

6. A method according to claim 4:
wherein the first lead and the second lead are a different configuration than the third lead.

7. A method according to claim 6:
wherein the third lead is an intramuscular lead and the first lead and the second lead are EMG leads.

8. A method according to claim 4:
further including recording electrical stimulation parameters used to activate the motor point of the first muscle and/or the motor point of the second muscle.

9. A method according to claim 4:
further including recording electrical stimulation parameters provided to the third lead to activate the motor point of the first muscle and the motor point of the second muscle.

10. A method according to claim 4:
wherein the first muscle comprises the middle deltoid muscle, and the second muscle comprises the posterior deltoid muscle, and the electrical stimulation applied to the third lead provides relief of shoulder pain.

11. A method according to claim 4:
further including removing the first lead and the second lead after placing the third lead.

12. A method according to claim 11:
wherein the electrical stimulation applied to the third lead provides relief of pain to both the first muscle and the second muscle.

* * * * *